(12) United States Patent
Courtney et al.

(10) Patent No.: US 10,699,411 B2
(45) Date of Patent: Jun. 30, 2020

(54) DATA DISPLAY AND PROCESSING ALGORITHMS FOR 3D IMAGING SYSTEMS

(71) Applicants: CONAVI MEDICAL INC., Toronto, ON (CA); SUNNYBROOK RESEARCH INSTITUTE, Toronto, ON (CA)

(72) Inventors: Brian Courtney, Toronto (CA); Neil Witcomb, Toronto (CA)

(73) Assignees: SUNNYBROOK RESEARCH INSTITUTE, Toronto, ON (CA); COLIBRI TECHNOLOGIES INC., Toronto, ON (CA)

( * ) Notice: Subject to any disclaimer, the term of this patent is extended or adjusted under 35 U.S.C. 154(b) by 0 days.

(21) Appl. No.: 15/726,998

(22) Filed: Oct. 6, 2017

(65) Prior Publication Data
US 2018/0158190 A1    Jun. 7, 2018

Related U.S. Application Data

(63) Continuation of application No. 14/777,092, filed as application No. PCT/CA2014/050283 on Mar. 17, 2014, now Pat. No. 9,786,056.

(Continued)

(51) Int. Cl.
| | | |
|---|---|---|
| *G06T 7/11* | (2017.01) | |
| *G06T 15/08* | (2011.01) | |
| *G06T 19/00* | (2011.01) | |
| *G06T 7/00* | (2017.01) | |
| *G06T 11/00* | (2006.01) | |

(Continued)

(52) U.S. Cl.
CPC .............. *G06T 7/11* (2017.01); *G06T 7/0012* (2013.01); *G06T 11/003* (2013.01); *G06T 15/08* (2013.01); *G06T 19/00* (2013.01); *A61B 8/466* (2013.01); *A61B 8/483* (2013.01); *G06T 2200/04* (2013.01); *G06T 2207/10101* (2013.01);

(Continued)

(58) Field of Classification Search
CPC ............ G06T 7/11; G06T 15/08; G06T 19/00
USPC ....................................................... 345/424
See application file for complete search history.

(56) References Cited

U.S. PATENT DOCUMENTS 6,002,738 A * 12/1999 Cabral .................. G06T 11/006
                                                    378/15
6,181,348 B1 * 1/2001 Geiger .................... G06T 17/10
                                                    345/423

(Continued)

FOREIGN PATENT DOCUMENTS

| EP | 2485194 A2 | 8/2012 |
|---|---|---|
| JP | 2009291295 A | 12/2009 |

*Primary Examiner* — Hai Tao Sun
(74) *Attorney, Agent, or Firm* — Hill & Schumacher

(57) ABSTRACT

The present disclosure provides methods to process and/or display data collected using 3D imaging probes. The methods include: a) methods for mapping a single 2D frame onto a 3D representation of a volume; b) methods for dynamically updating portions of a 3D representation of a volume with a high temporal resolution, while leaving the remainder of the volume for contextual reference; c) methods for registering volumetric datasets acquired with high temporal resolution with volumetric datasets acquired with relatively low temporal resolution in order to estimate relative displacement between the datasets; and d) methods for identifying structures within a volume and applying visual cues to the structures in subsequent volumes containing the structures.

14 Claims, 19 Drawing Sheets

Related U.S. Application Data

(60) Provisional application No. 61/801,284, filed on Mar. 15, 2013.

(51) Int. Cl.
*A61B 8/08* (2006.01)
*A61B 8/00* (2006.01)

(52) U.S. Cl.
CPC ............... *G06T 2207/10132* (2013.01); *G06T 2207/30068* (2013.01); *G06T 2210/41* (2013.01)

(56) References Cited

U.S. PATENT DOCUMENTS

| | | | |
|---|---|---|---|
| 6,750,873 B1* | 6/2004 | Bernardini | G06T 15/04 345/581 |
| 8,057,394 B2* | 11/2011 | Dala-Krishna | A61B 8/0883 600/466 |
| 8,622,915 B2* | 1/2014 | Dala-Krishna | A61B 8/0883 600/466 |
| 2004/0070582 A1* | 4/2004 | Smith | A61B 8/4254 345/419 |
| 2004/0153128 A1* | 8/2004 | Suresh | G06F 19/3481 607/14 |
| 2005/0237336 A1* | 10/2005 | Guhring | G06T 15/04 345/582 |
| 2007/0238999 A1* | 10/2007 | Specht | A61B 5/02007 600/437 |
| 2008/0146932 A1* | 6/2008 | Chalana | A61B 5/204 600/447 |
| 2008/0221446 A1 | 9/2008 | Washburn et al. | |
| 2008/0249414 A1* | 10/2008 | Yang | A61B 8/483 600/445 |
| 2009/0201291 A1* | 8/2009 | Ziv | A61B 5/055 345/424 |
| 2010/0195881 A1* | 8/2010 | Orderud | A61B 8/08 382/131 |
| 2011/0071395 A1* | 3/2011 | Miller | A61B 8/0883 600/439 |
| 2013/0303887 A1* | 11/2013 | Holsing | A61B 1/2676 600/424 |
| 2014/0071125 A1* | 3/2014 | Burlina | G06T 17/00 345/420 |
| 2014/0152653 A1* | 6/2014 | Dala-Krishna | A61B 8/0883 345/419 |
| 2016/0253826 A9* | 9/2016 | Ziv | A61B 5/055 382/131 |

\* cited by examiner

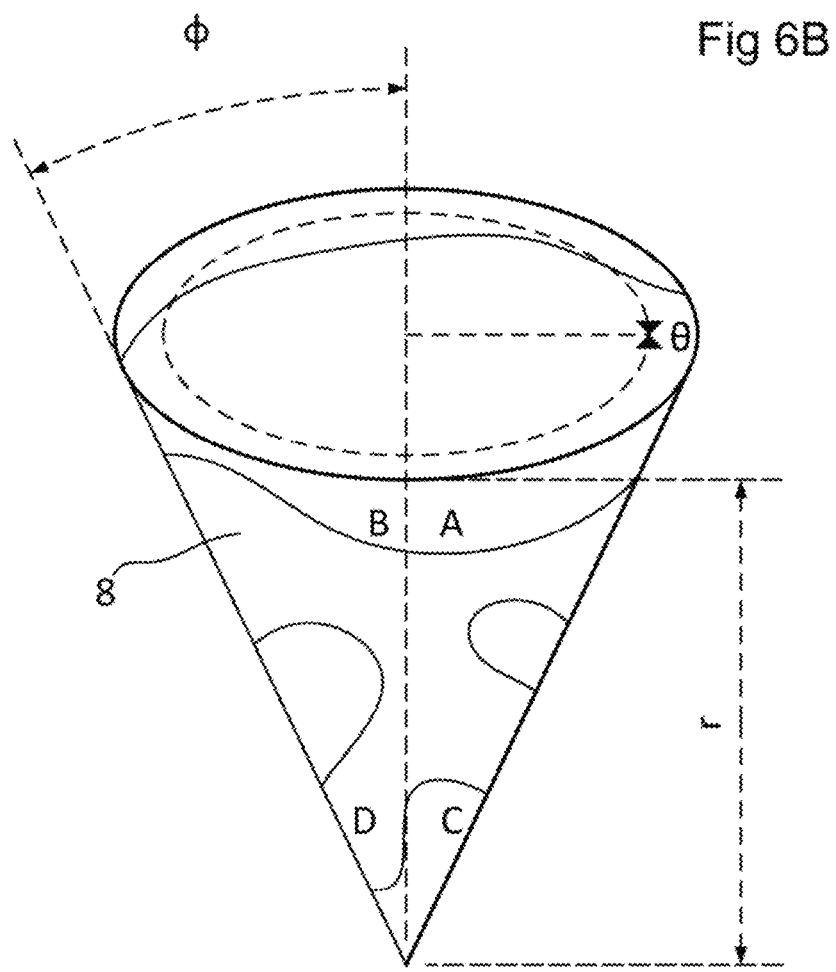

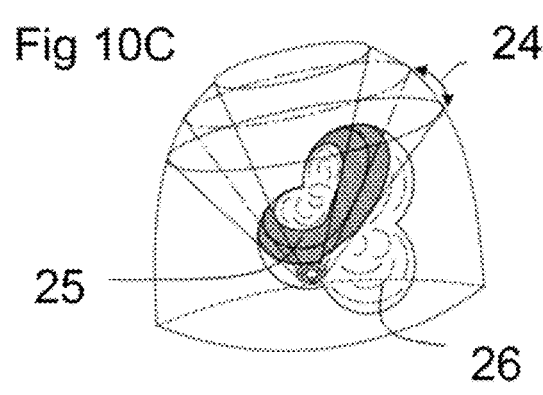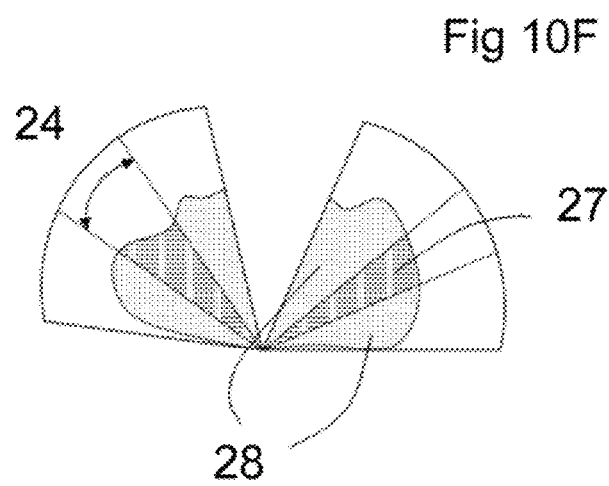

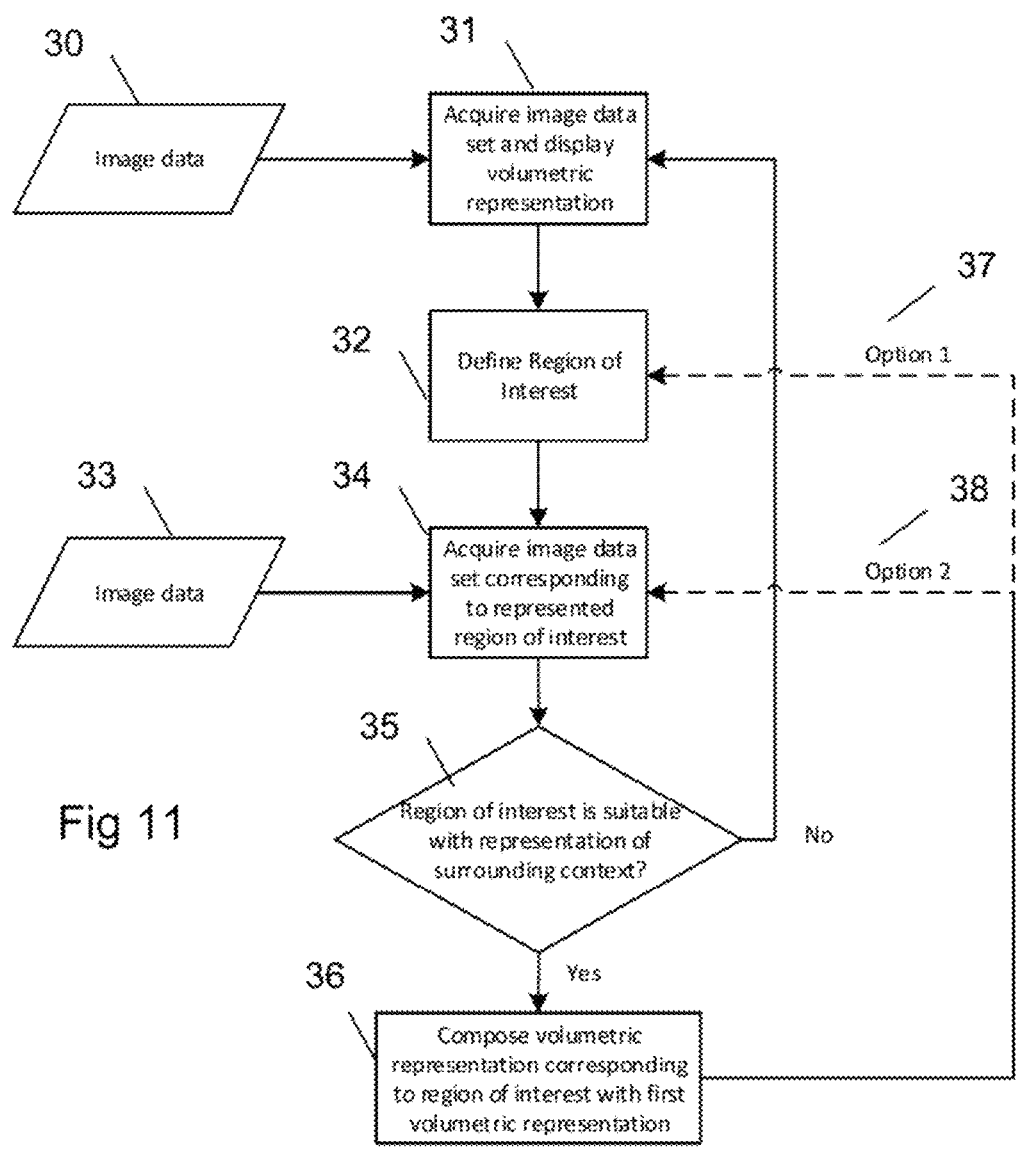

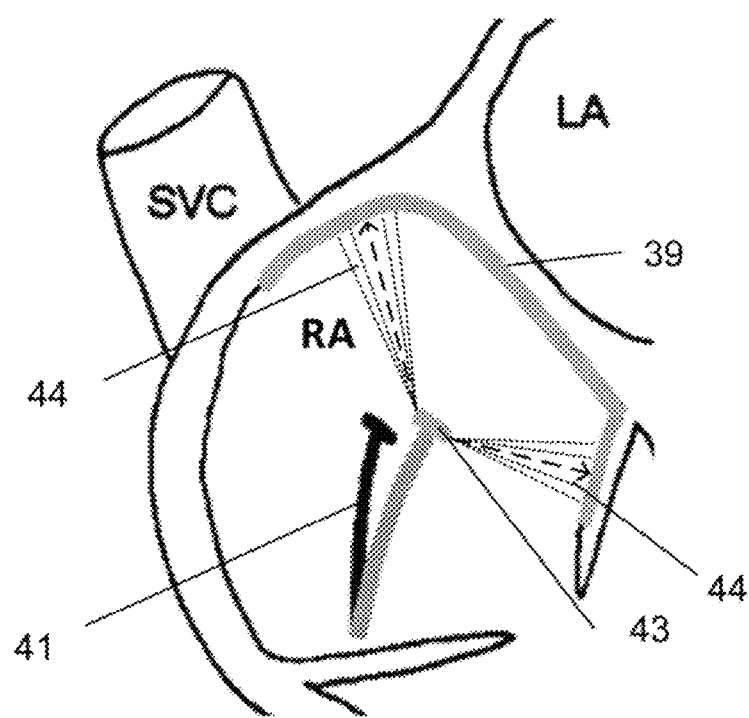

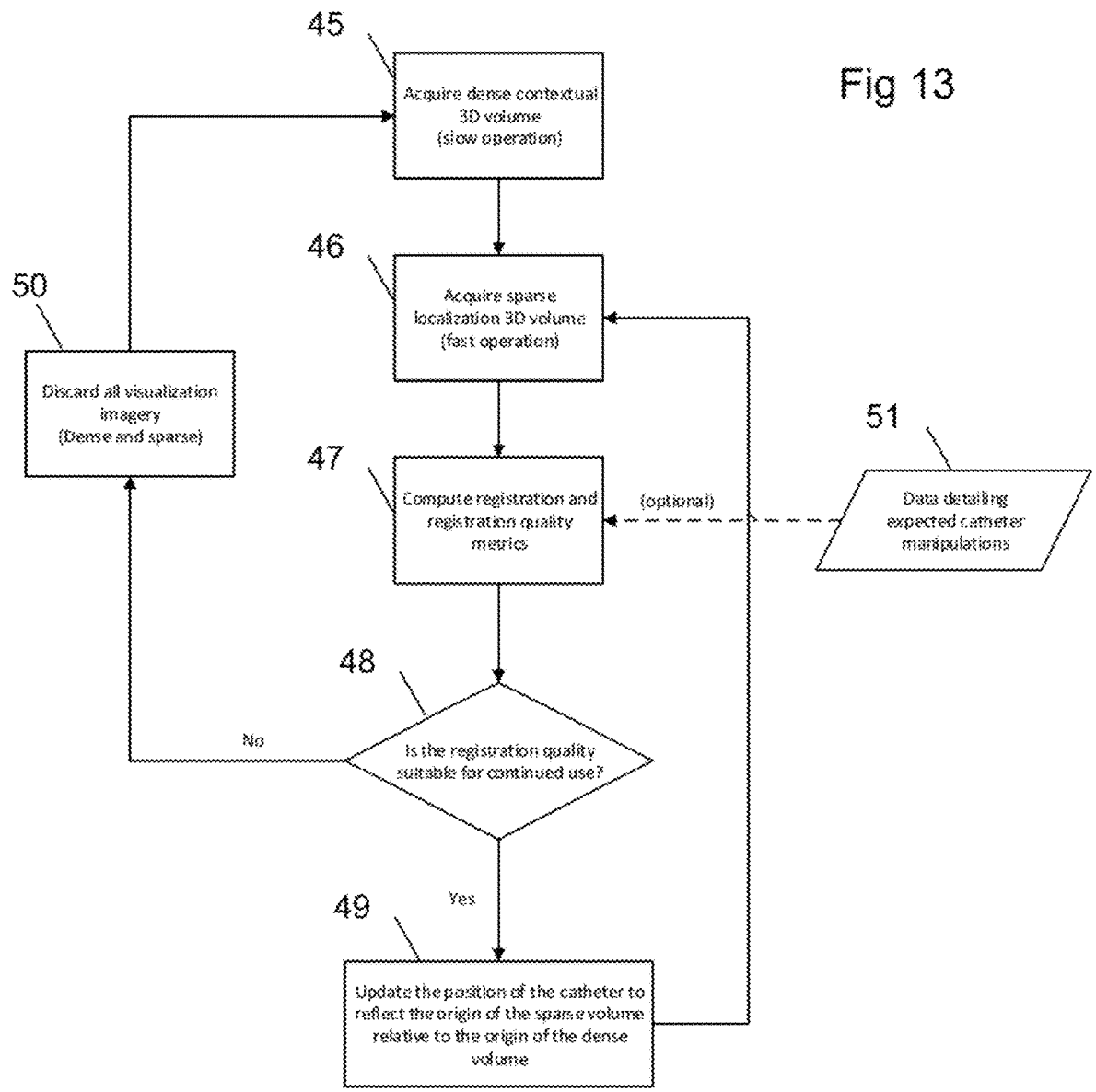

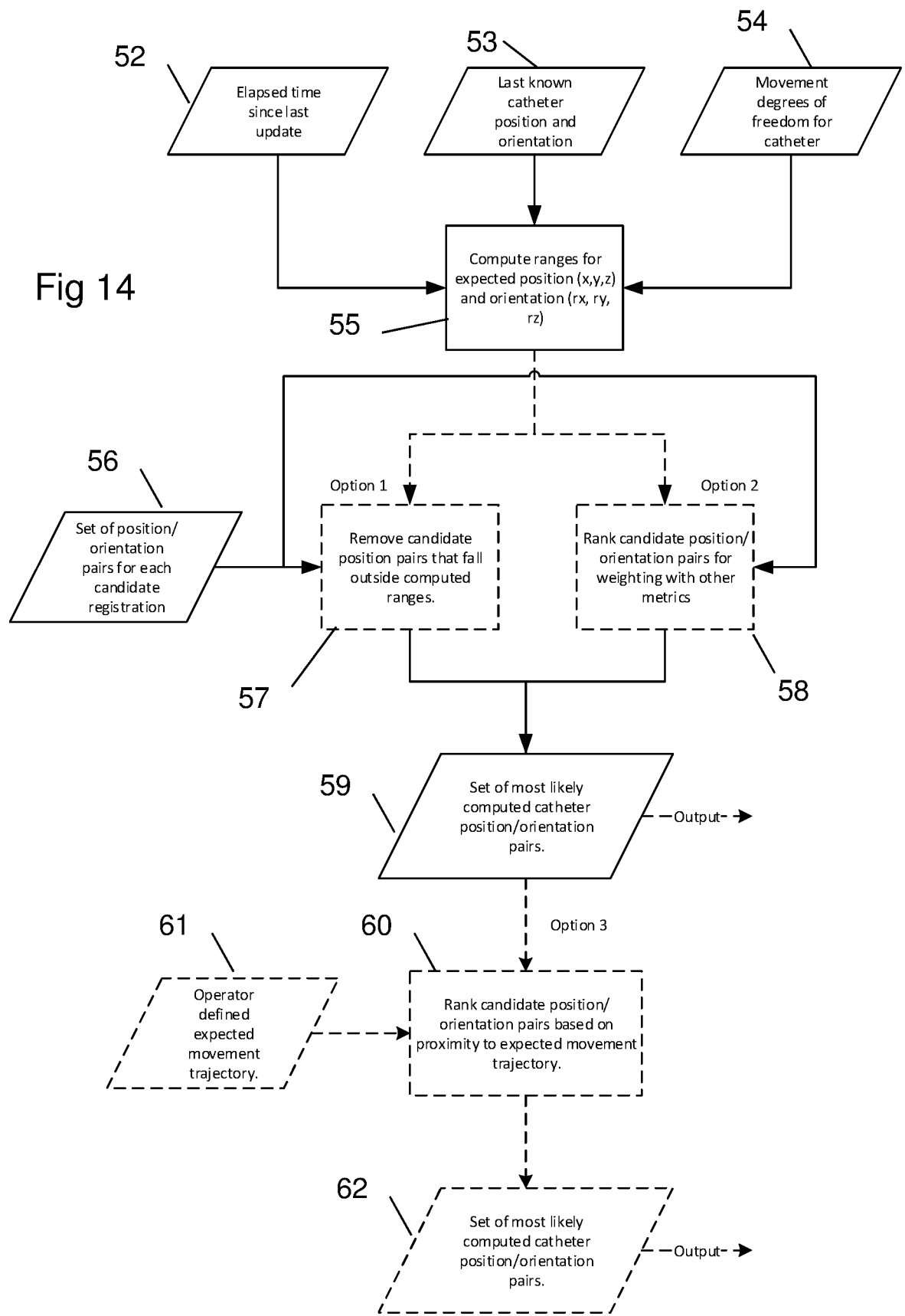

DATA DISPLAY AND PROCESSING ALGORITHMS FOR 3D IMAGING SYSTEMS

FIELD

The present disclosure relates generally to the field of imaging probes for imaging mammalian tissues and structures, including minimally invasive imaging by ultrasound and optical coherence tomography. More particularly the present disclosure relates to methods (embodied as algorithms) to process and/or display data collected using 3D imaging probes.

BACKGROUND

Imaging of the body serves multiple purposes, including any of i) assessing tissue structures and anatomy; ii) planning and/or guiding interventions on localized regions of the body; and iii) assessing the result of interventions that alter the structure, composition or other properties of the localized region. Ultrasound and optical imaging techniques can be very useful for a variety of minimally invasive applications, including intravascular and intracardiac procedures. By way of example, two particularly important implementations of minimally invasive ultrasound are intravascular ultrasound (IVUS), for imaging blood vessels, and intracardiac echocardiography (ICE) for imaging cardiac chambers. Both ICE and IVUS are minimally invasive, and involve placing one or more ultrasound transducers inside a blood vessel or cardiac chamber to take high quality images of these structures.

Optical imaging methods based on fiber optic technology used in the field of medicine include optical coherence tomography, angioscopy, near infrared spectroscopy, Raman spectroscopy and fluorescence spectroscopy.

Imaging probes can be configured using mechanically scanning mechanisms where the direction of the energy beams used to generate images is determined by the mechanical motion of one or more components responsible for the emission and/or sensing of imaging energy. Imaging probes can also be constructed using arrays of imaging elements, such as phased array ultrasound imaging probes and fiber optic bundles or charge coupled devices used in various optical imaging devices such as angioscopes, endoscopes and laryngoscopes.

Examples of 3D scanning mechanisms are provided in U.S. Pat. No. 8,214,010 ("Scanning mechanisms for imaging probe", Courtney et al), the entirety of which is herein incorporated by reference.

Areas of application for 3D minimally invasive imaging include image guidance for procedures in structural heart disease and electrophysiology procedures. It is often necessary to place catheters within specific positions in the cardiac chambers in order to perform a therapeutic maneuver, such as the implantation of a device (such as a closure device for patent foramen ovales, valvular repair or replacement devices, left atrial appendage closure devices) or the placement of a therapeutic catheter (such as an ablation or cryotherapy catheter). It may also be necessary to guide intermediate steps in a procedure, such as crossing the atrial septum of the heart. The use of minimally invasive imaging can facilitate these steps. 3D intracardiac echo (3D ICE), is one such technology for this purpose.

SUMMARY OF RELATED ART

Suorsa et al (U.S. Pat. No. 6,315,732) describe a catheter for intravascular delivery that has an ultrasound transducer that can pivot around an axis other than the longitudinal axis of the catheter by means of a cable system and collect 3D images.

Maroney et al (U.S. Pat. No. 5,373,849) and Gardineer (U.S. Pat. No. 5,373,845) also describe 3D ultrasound imaging catheters.

Hossack et al (WO/2006/121851) describe a forward looking ultrasound transducer using a capacitive micromachined ultrasound transducer (CMUT) and a reflective surface.

Courtney et al (U.S. Pat. No. 8,214,010) describes 3D scanning mechanisms using mechanically scanned single element imaging devices that can be used to generate 3D imaging datasets using ultrasound and/or optical imaging methods. A mechanical device such as the one described has the advantage of being able to image a field of view that is larger than what is typically characteristic of a 2D array imaging device. This is particularly true of in the case of ultrasound imaging. The imaging data sets collected with the devices described therein can be described in spherical coordinates and/or Cartesian coordinates. The data collected by the scanning mechanisms described by Courtney et al in U.S. Pat. No. 8,214,010 are collected in spherical coordinates, and the volumetric imaging dataset can be described as a function of Cr ('r', ($\Theta$), 'phi' ($\Phi$)) where 'r' is a radius, 'theta' ($\Theta$) is an angle of rotation around a rotary axis and 'phi' ($\Phi$) is an angle of tilt. In several of the embodiments in U.S. Pat. No. 8,214,010, the imaged volume is scanned as follows:

1) Radius 'r' is calculated based on the time of flight of ultrasound or light through the region being imaged. In some embodiments, 'r' is the most frequently scanned or imaged dimension of the spherical coordinate system.
2) Angle 'theta' ($\Theta$) is based on the angle of rotation of an imaging assembly around a rotational axis of the imaging assembly. In many embodiments, angle 'theta' ($\Theta$) represents the angular displacement caused by rotary motion of a rotary drive mechanism, mechanically coupled to a rotary shaft that, in turn, is mechanically coupled to the imaging assembly. In some embodiments, angle 'theta' ($\Theta$) is the second most frequently scanned dimension of the spherical coordinate system. In other embodiments, angle 'theta' ($\Theta$) is the least frequently scanned dimension of the spherical coordinate system.
3) Angle 'phi' ($\Phi$) is most frequently referred to as the "imaging angle" in U.S. Pat. No. 8,214,010. In some embodiments, angle 'phi' ($\Phi$)) is the least frequently scanned dimension of the spherical coordinate system. In other embodiments, angle 'phi' ($\Phi$)) is the second most frequently scanned dimension of the spherical coordinate system.

In the context of minimally invasive imaging, an advantage of some embodiments of the scanning mechanisms described in U.S. Pat. No. 8,214,010 includes a potentially wide field of view, where radius 'r' can range from several hundred microns to over 10 centimeters, angle 'theta' ($\Theta$) can range from 0 to 360 degrees (usually in a repeated pattern) and 'phi' ($\Phi$)) can span a broad range of angles, and for many forward-looking embodiments could span from 0 to 90 degrees or more. Another advantage includes the ability to perform 3D imaging. Another advantage includes the ability to collect 4D imaging by using gating techniques including ECG gating to capture repeated motion of dynamic structures such as regions of a beating heart.

Regarding structures that undergo motion, such as a beating heart, the geometric accuracy and/or image quality is dependent on the speed at which such structures are imaged relative to the speed of motion that they experience. For example, in 2D imaging, higher refresh rates of the images improve geometric accuracy of measurements made within the 2D image. Similarly, in 3D imaging, reconstructions of regions of imaged structures are more likely to be less influenced by motion if said regions are imaged within shorter spans of time unless suitable motion compensation algorithms, such as ECG gating are employed.

SUMMARY

The present disclosure provides display means for providing 3D reconstructions of images of mammalian tissues and structures acquired using minimally invasive imaging probes, including ultrasound and/or optical imaging techniques. More particularly the present disclosure relates to methods of display of images collected using scanning mechanisms that collect imaging data by scanning, sampling and/or otherwise collecting data across two angles and a linear dimension.

Given that some embodiments of the scanning mechanisms described in U.S. Pat. No. 8,214,010 have a fastest scanning rate along the radial dimension, followed by a slower scanning rate along the first angular dimension 'theta' ($\Theta$), followed by yet a slower scanning rate along the second angular dimension 'phi' ($\Phi$)), the present disclosure provides methods for image display that present a subset of 3D imaging data collected along the two dimensions that are scanned most frequently (and thus least prone to motion artifacts), which in many cases will be radius 'r' and angle 'theta' ($\Theta$).

The present disclosure also provides methods for image display wherein subsets of the 3D imaging data collected along the dimensions that are scanned most frequently are displayed in combination with 3D reconstructions of all or a portion of 3D imaging data.

The present disclosure also teaches how to identify regions of a texture map superimposed on a 3D reconstruction that can be made more transparent and facilitate visualization of inner structures of the 3D reconstruction that would otherwise be obstructed by the surface onto which a 2D image texture is mapped.

The present disclosure also provides methods for the operator to sweep through a range of subsets of the angle 'phi' ($\Phi$)) through the 3D reconstruction.

The present disclosure provides methods for image display where the 3D imaging data is processed to facilitate visualization of regions of the 3D imaging data that are more commonly associated with being relatively transparent to the imaging modality, such as the chambers or vascular lumens of the heart using ultrasound, wherein blood is relatively more transparent than myocardium and other cardiac tissues. For example, such methods would be useful in situations when the morphology and/or structure of the chambers and/or vascular lumens is of more interest to the operator than the morphology and/or structure of the other surrounding structures.

The present disclosure also describes methods for displaying a 3D reconstruction of a 3D volume and further displaying a more frequently updated reconstruction of a subset of the 3D volume. For example, this would provide a combination of contextual information from the larger 3D volume, while providing imaging information with greater temporal resolution within the more frequently updated subset of the 3D volume.

The present disclosure further describes methods to parametrically determine when a contextual 3D volume should be updated after a period of time in which a subset of the 3D volume has been imaged and it is determined that the contextual 3D volume may no longer adequately represent the region surrounding the more frequently scanned subset of the 3D volume. Such determination may be made as a result of alteration of the surrounding structures and/or motion of the surrounding structures and/or displacement of the imaging probe within the surrounding structures or for other reasons.

The present disclosure also describes methods that display a less recently acquired portion of a 3D volume in a visibly recognizable format than more recently acquired portions of a 3D volume so that the operator can identify anatomic landmarks and other structures within the 3D volume while also recognizing which portion of the 3D volume has been most recently updated and hence, most representative of the region imaged at the point in time of image display.

The present disclosure teaches using the 3D imaging capabilities of the imaging system and imaging probe to identify the location and/or orientation of a portion of the imaging probe within a 3D volume.

The present disclosure teaches using the imaging capabilities of the imaging system and imaging probe in combination with localization algorithms to update the location and/or orientation of a portion of the imaging probe within a 3D volume imaged previously.

The present disclosure teaches using the imaging capabilities of the imaging system and imaging probe in combination with localization algorithms to determine when the location and/or orientation of a portion of the imaging probe within a previously acquired 3D volume can no longer be determined with acceptable reliability.

An embodiment provides a method for forming a composite visual display of a volume, from a set of imaging data of a volumetric representation of the volume and a single 2D imaging frame, comprising the steps of:

a) receiving a set of imaging data from the volume;

b) selecting a single 2D imaging frame from the set of imaging data;

c) processing said set of imaging data to produce a modified volume representation such that all image data on a selected side of said single 2D imaging frame are excluded from the volumetric representation; and d) mapping the 2D imaging frame to an appropriate location on the modified volume representation.

There is also provided a method for forming a composite visual display, from a plurality of volumetric image data sets, comprising the steps of:

a) receiving a first volumetric image data set of a first volume obtained over a first time interval using a mechanically scanned imaging device, processing said first volumetric image data set to reconstruct a representation of the first volume;

b) defining a region of interest within the first volume;

c) receiving an additional image data set of the region of interest obtained over a second time interval shorter than the first time interval;

d) combining the additional image data set of the region of interest with the first volumetric image data set to produce a combined image data set, and processing the combined data set to reconstruct a combined representation of the first volume, and displaying the combined representation, wherein the representation of the region of interest portion of the first volume is updated more frequently than the remainder of the first volume; and e) repeating steps b) through d) zero or more times.

There is also provided a method for calculating changes to a position and/or orientation of an imaging device during acquisition of multiple images of a volume, comprising the steps of:

a) receiving a first set of imaging data from a first volume acquired over a first time interval with the imaging device;

b) processing said first set of imaging data from the first volume to reconstruct a representation of the first volume suitable for display;

c) receiving an additional set of imaging data from an additional volume acquired over an additional time interval shorter than said first time interval with the imaging device;

d) processing said additional set of imaging data to reconstruct a representation of the additional volume;

e) processing the representation of the first volume with the representation of the additional volume to register the representation of the first volume with the representation of the additional volume, and including applying a goodness fit to the registered representations;

f) wherein in the event an acceptable goodness of fit is achieved, computing a position and/or orientation of the imaging device during acquisition of the additional set of imaging data relative to a position and/or orientation of the imaging device during acquisition of the first set of imaging data, and repeating steps c) through e) zero or more times; and g) in the event registration is not achieved repeat steps a) through e) zero or more times.

There is also provided a method for identifying and highlighting a region in a volume during multiple scans of the volume, comprising the steps of:

a) acquiring an image set of a first volume and producing a 3D representation of the first volume from the image set;

b) identifying a region of interest in the 3D representation of the first volume;

c) characterizing the region of interest with a set of parameters and storing the set of parameters of the characterized region;

d) applying a visualization cue to the characterized region of interest;

e) acquiring an additional image set of an additional volume and producing a 3D representation of the additional volume from the additional image set;

f) searching the additional image set using the stored set of parameters of the characterized region of interest to identify in the additional volume a presence of the region of interest;

g) in the event the region of interest is identified in the additional volume then optionally updating the stored set of parameters in step c) and repeating steps d) to f) zero or more times; and h) in the event the region of interest is not identified in the additional volume then repeating steps a) to g) zero or more times.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 6A and 6B depict an example of processing imaging data from a single revolution of angle 'theta' ($\Phi$) and mapping the imaging data to a cone-like surface;

FIGS. 10A through 10F depict example visualizations of volumetric imaging data for which a subset of the volume may be updated more frequently than the remainder of the volume;

FIG. 11 shows a flow chart highlighting the important operations employed when generating a visualization combining frequently acquired image data with a static 3D volumetric representation;

FIGS. 12A through 12C depict an embodiment of volume registration using a dense static volume and a sparse dynamic volume;

FIG. 13 shows a flow chart highlighting operations employed in an example embodiment of spare-to-dense volume registration;

FIG. 14 shows a flow chart showing an example of methods that may be used to estimate likely position and orientation information.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

As used herein, the phrase "co-registration of images" refers to the process of identifying a subset of imaging data acquired by one set of imaging parameters with a subset of imaging data acquired using another set of imaging parameters (i.e. modality, time, spatial location, imaging conditions, etc.) where the identified imaging data from the two sets of imaging parameters were acquired by detecting a form or forms of imaging energy (e.g. photons or ultrasound) from the same object (i.e. tissue, devices or other structures of interest). Each co-registered point in the first subset can then be mapped to a corresponding point in the second subset such that the two points are thought to have been acquired from a similar focal region of the imaged object (or tissue). Successful and accurate co-registration of images, or portions thereof, between sets of imaging parameters is helpful in that it can provide multiple opportunities to assess features of interest of the imaged object by more than one set of imaging parameters.

Figure 16:
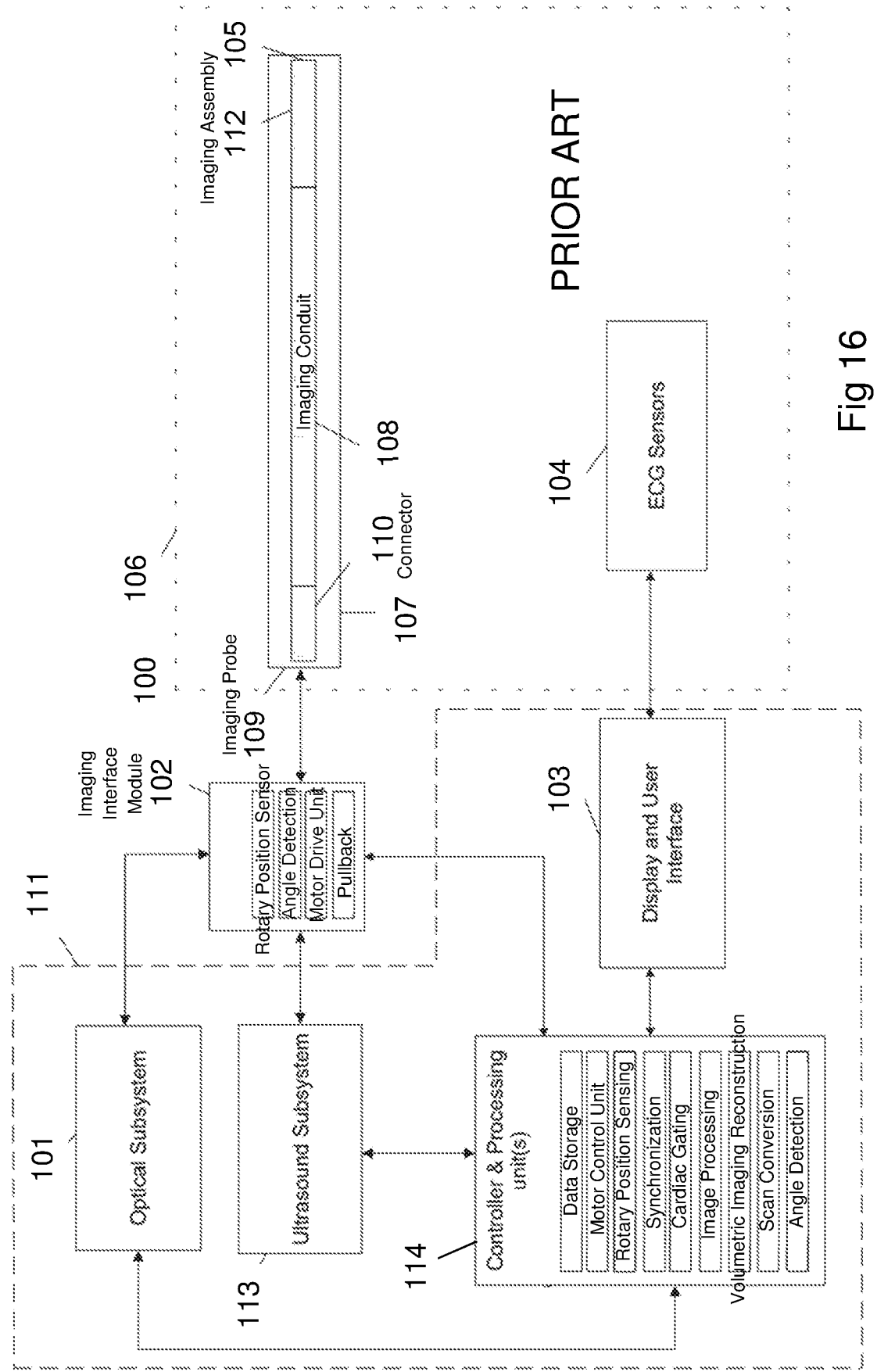
FIG. 16 is a schematic of an imaging system for either ultrasound imaging, optical imaging or both.

The various embodiments discussed in this disclosure relate to an imaging system for either ultrasound imaging, optical imaging or both. Referring first to FIG. 16, an imaging system is shown at 100 comprising imaging probe 107, which connects via patient interface module 102 to image processing and display system 111. Image processing and display system 111 comprises hardware to support one or more imaging modalities, such as ultrasound, optical coherence tomography, angioscopy, infrared imaging, near infrared imaging, Raman spectroscopy-based imaging, or fluorescence imaging.

Texture-Mapped to Clipped Volume Composite Display

Figure 1:
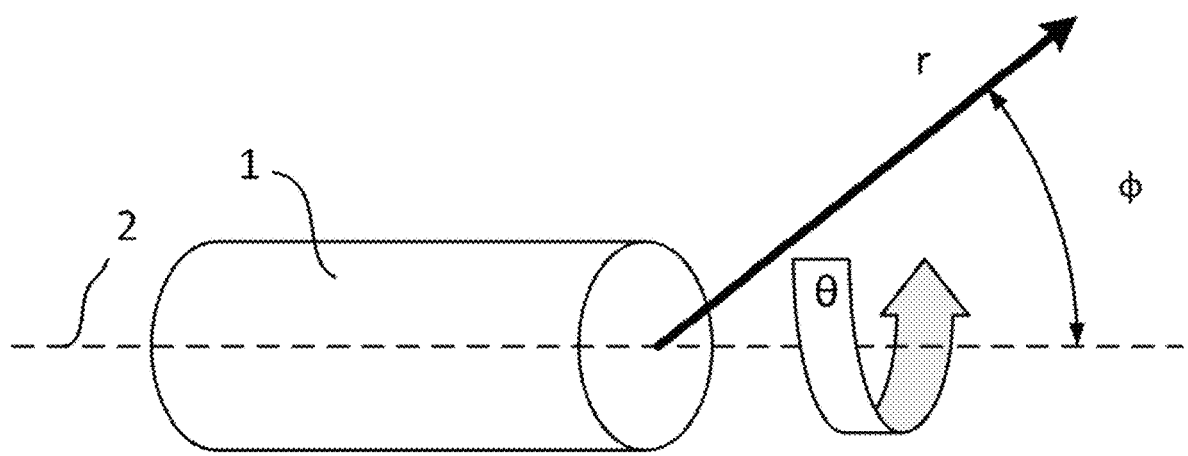
FIG. 1 depicts an example spherical coordinate system in relation to an embodiment of the present disclosure.
Figure 2:
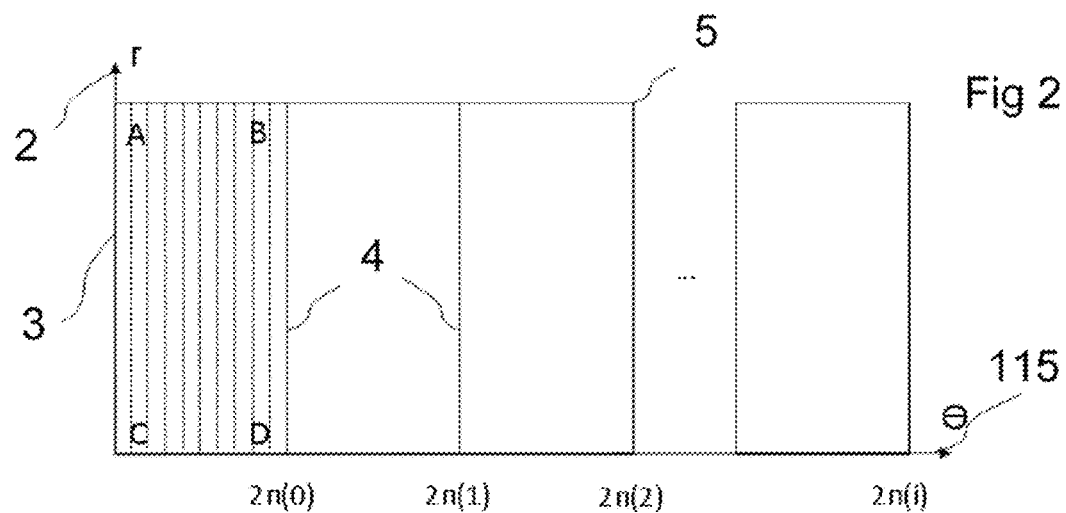
FIG. 2 shows a relation of contiguous imaging data to image frames described using the spherical coordinate system of the present disclosure.

FIG. 1 depicts a spherical coordinate system that can be used to describe a set of imaging data acquired from a volume using an imaging assembly 1. For example, a sequence of intracardiac echo (ICE) data samples collected along 'r' can be represented as a one-dimensional image of N unique picture elements (pixels), with each element corresponding to a unique sampling of ultrasound data. The spatial length of 'r' corresponds to the imaging depth of the image transducer and may consequently define the spacing between pixels as being equal to r/N in the case of uniform sampling. Successive 1D imaging data vectors are acquired as the imaging assembly moves around the rotational axis 2 (measured by 'theta' ($\Phi$)). FIG. 2 depicts a collection of successively acquired 1D imaging data vectors 3 arranged according to increasing rotational angle 'theta' ($\Theta$). Embodiments may treat this arrangement as a two-dimensional image 5, with picture elements along the 'r'-axis 2 representing imaging data samples at increasing distances from the imaging assembly and picture elements along the θ-axis 115 representing imaging data samples at increasing angles around the rotational axis of an imaging assembly.

This continuous collection and arrangement of imaging data would result in a pixel matrix with an ever increasing width. This representation is also appropriately described as a temporal arrangement with the oldest sampled vectors lying at the left edge of FIG. 2 and the newest being continuously added on the right. Note that the θ-axis 115 ('theta') does not necessarily have a linear relationship with time, as the rotational velocity may vary with time, such as to change the tilt angle (represented as 'phi' ($\Phi$) in FIG. 1) of an imaging beam. Practical embodiments may divide the large two-dimensional array of acquired samples into imaging frames 4 corresponding to complete revolutions of the imaging assembly ('theta' ($\Theta$) ranging from 0 to 2 pi radians). Single 2D imaging frames need not be restricted to having a fixed tilt angle of 'phi' ($\Phi$).

Figure 3:
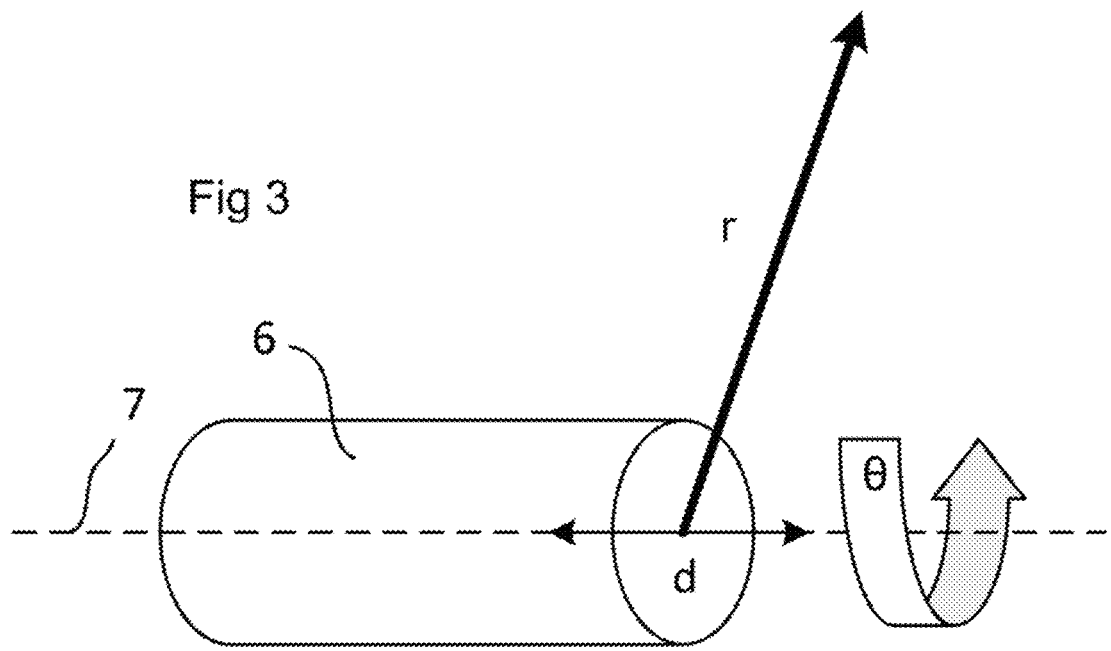
FIG. 3 depicts an example cylindrical coordinate system in relation to an embodiment of the present disclosure.

FIG. 3 depicts an alternate configuration of an imaging assembly 6 where the tilting degree of freedom described by 'phi' ($\Phi$) in FIG. 1 is removed and a longitudinal degree of freedom d is added. Imaging data is again collected along vector 'r' as the imaging assembly rotates about 7 (the corresponding angle represented as 'theta' ($\Theta$)) while the entire assembly is translated along 7 (the corresponding distance represented by 'd') resulting in the collection of imaging data from a cylindrical volume. It is to be understood that while axis 7 is shown as a straight line, in the case of flexible imaging catheters, axis 7 may be a curved path, as is common in the practice of intravascular imaging and pullback acquisitions.

Figure 4:
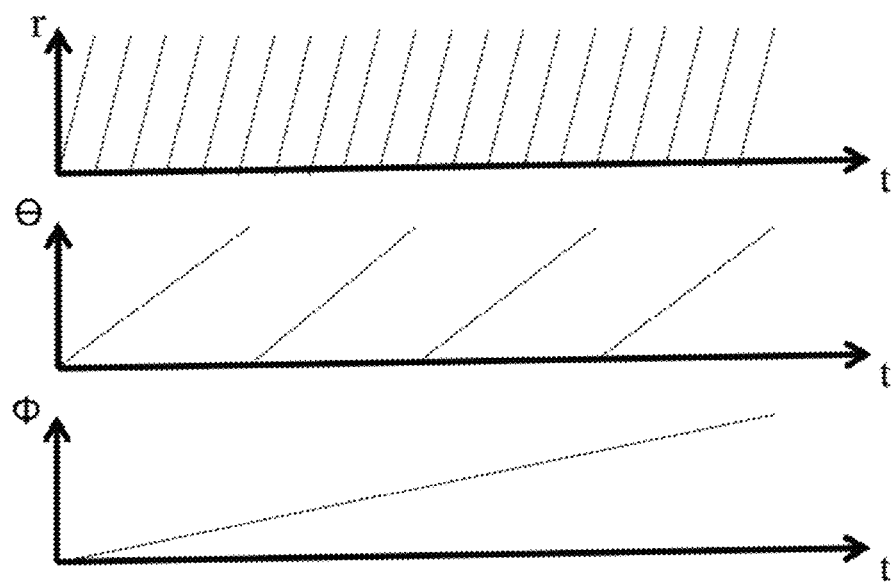
FIG. 4 shows a temporal relationship between three acquisition axes of one possible configuration of the present disclosure.

FIG. 4 depicts the relative temporal relationship between data acquisition along each of the three imaging axes which is characteristic of many embodiments. Acquisition along the radial axis 'r' is fastest followed by acquisition about the longitudinal axis 'theta' ($\Theta$) followed again by acquisition along the tilt axis 'phi' ($\Phi$)), which may typically be the slowest.

Figure 5:
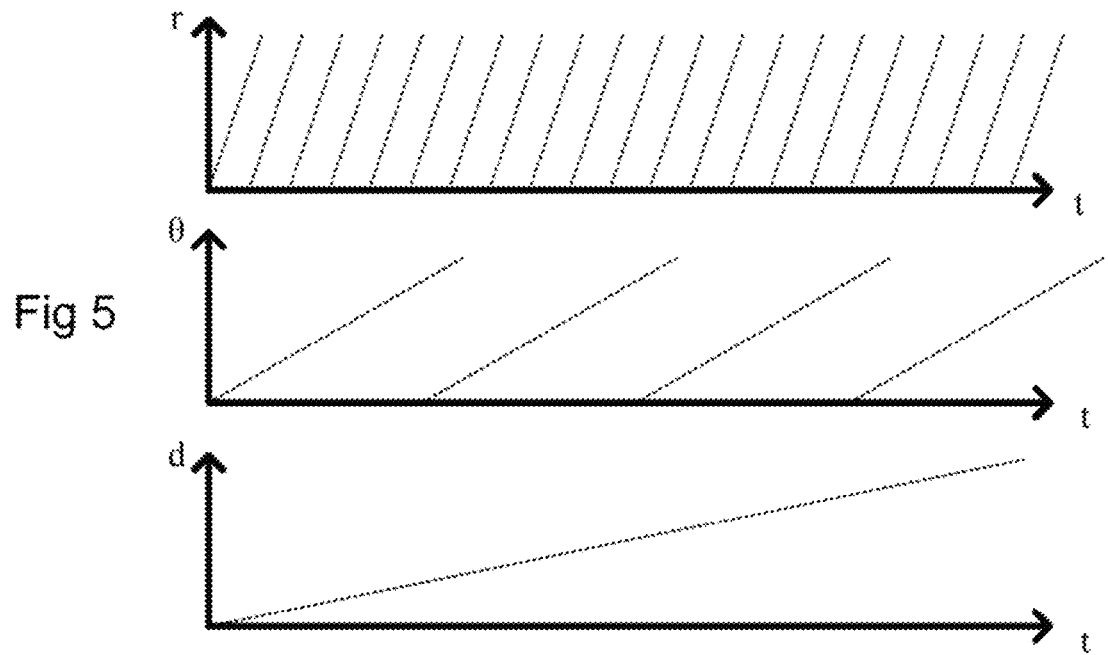
FIG. 5 shows a temporal relationship between three acquisition axes of an alternative configuration the present disclosure.

FIG. 5 depicts an analogous temporal relationship reflecting the configuration depicted in FIG. 3 with the collection of data along longitudinal axis 'd' being typically the slowest.

Figure 6A:
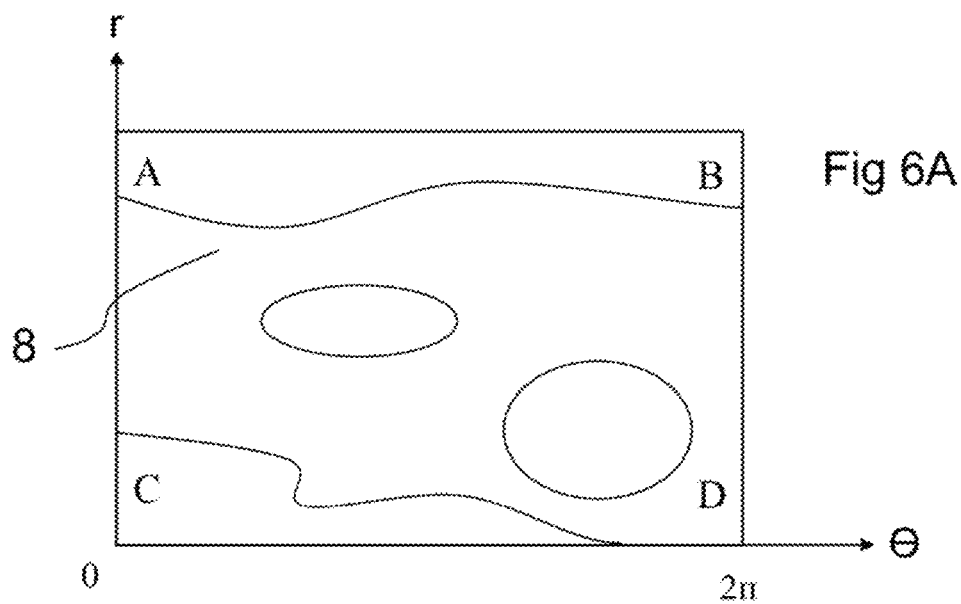

By incorporating the imaging angle 'phi' ($\Theta$), a frame of 2D image data 8 can be represented in a three dimensional manner that reflects the physically travelled path of an energy beam that is emitted from and/or received by an imaging assembly. FIG. 7B depicts said travelled path for a number of revolutions about fixed angles of 'phi' ($\Phi$)) and FIG. 7C depicts the travelled path during an acquisition where the tilt angle varies smoothly. FIG. 6A depicts an acquired 2D image frame produced by a single revolution of the imaging assembly covering the range of possible 'theta' ($\Theta$) values while angle 'phi' ($\Phi$)) is constant. FIG. 6B then depicts a possible embodiment using the same acquired imaging data frame 8 providing a visual representation of the rotational angle 'theta' ($\Theta$) and fixed tilt angle 'phi' ($\Phi$). In this representation, the 2D imaging data frame is mapped to a wireframe conical geometry (defined by 'r', 'theta' ($\Theta$) and 'phi' ($\Phi$)) that is representative of the region sampled within the volume during acquisition by the imaging device.

U.S. Pat. No. 8,214,010 describes potential embodiments where acquired image data is reconstructed into a 3D volume representation with spatial extents spanning ranges of spherical coordinate dimensions 'r', 'theta' ($\Theta$) and 'phi'

(Φ)). Some embodiments of the present disclosure extend upon those visualization embodiments for 3D reconstructions by creating composite volumetric representations of imaging data sets that incorporate texture mapping of 2D imaging data frames. Other embodiments of the present disclosure incorporate means of representing 3D reconstructions for image data sets acquired using the imaging assembly depicted in FIG. 3.

Figure 8A:
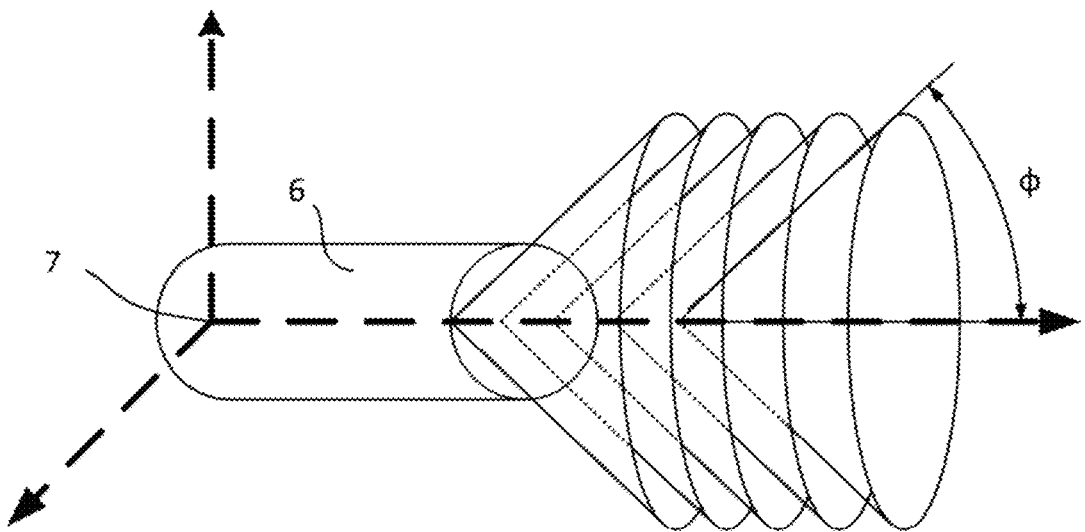
FIGS. 8A and 8B depict examples of imaging systems capable of imaging a cylindrical volume of space along the length axis of the cylinder in discrete and continuous motions respectively.
Figure 8B:
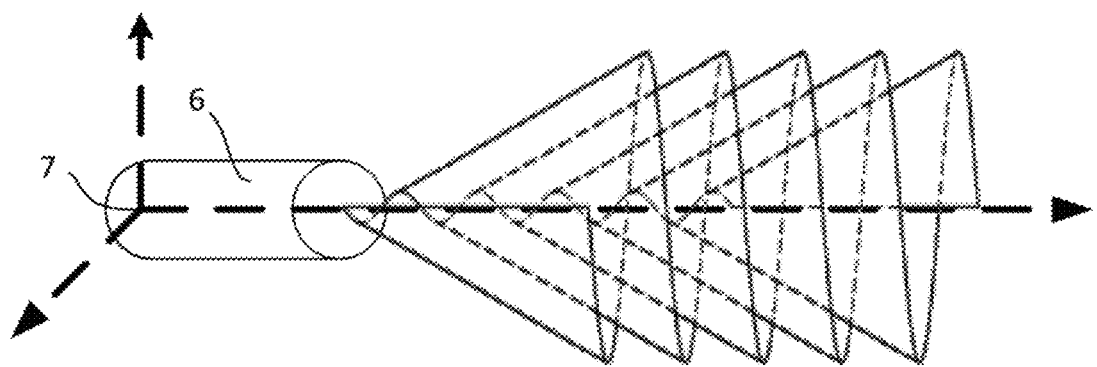
Figure 8C:
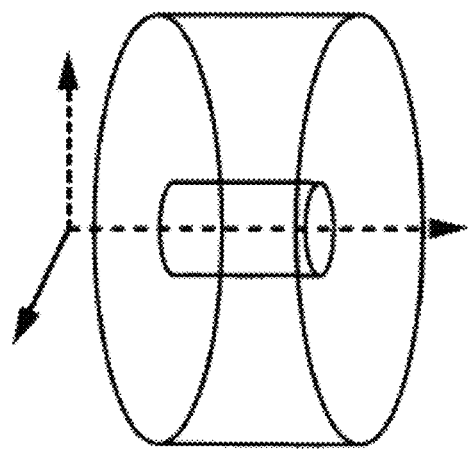
FIG. 8C depicts the volumetric image extents acquired during a scan of one embodiment of the imaging system for which the present disclosure is adapted to incorporate.

FIG. 8A depicts the acquisition of image data as the imaging assembly 6 is pulled along the longitudinal axis 7. The angle of the transducer is fixed at an angle 'phi' (Φ)) typically (but not necessarily) close to ninety degrees measured from the longitudinal axis 7. A reconstructed volumetric representation of data acquired along such a trajectory would reside within a volume that resembles a cylinder. In this case, the data is acquired in fixed increments along the longitudinal axis 7. The continuous acquisition of imaging data while the imaging assembly 6 moves along the longitudinal axis 7 at a constant rate would result in the collection pattern depicted in FIG. 8B. Volumetric representations can be created in a similar fashion for each of the depicted acquisition trajectories.

Figure 7A:
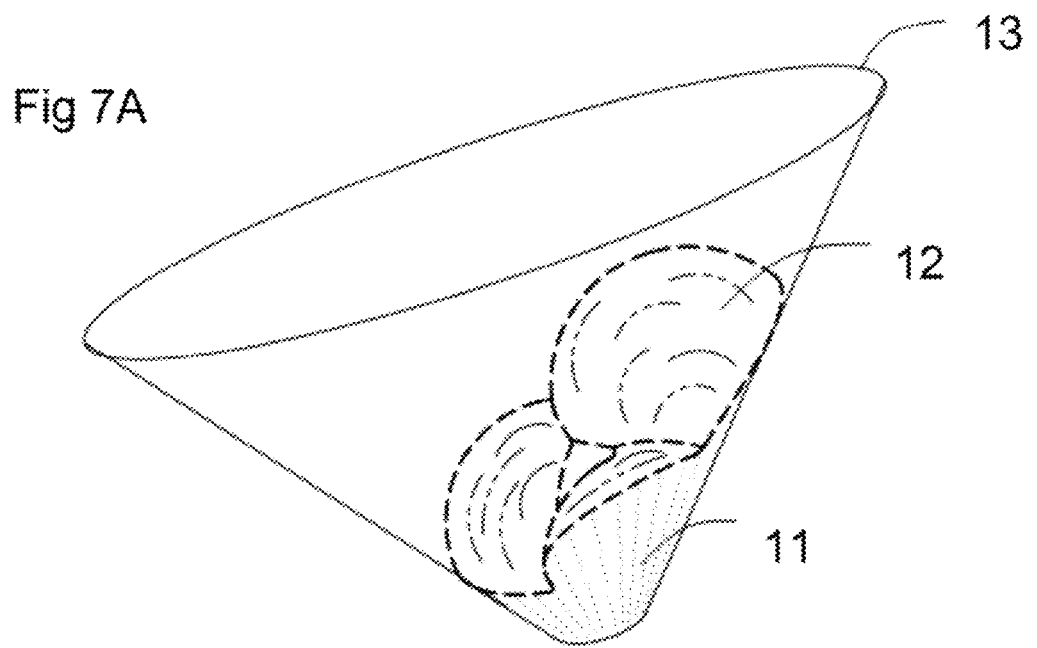
FIGS. 7A and 7D depict a visualization embodiment of both volumetric data and conical surface for the present disclosure.
Figure 7B:
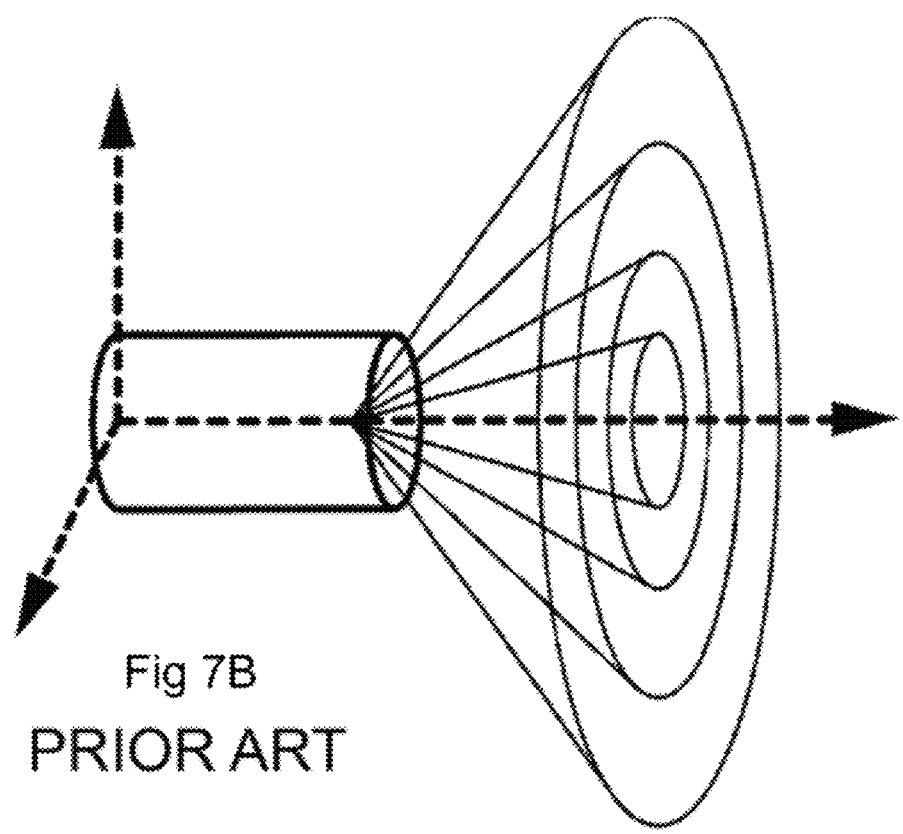
FIGS. 7B and 7C depict examples of imaging systems capable of forward viewing for which the present disclosure is adapted to incorporate.
Figure 7C:
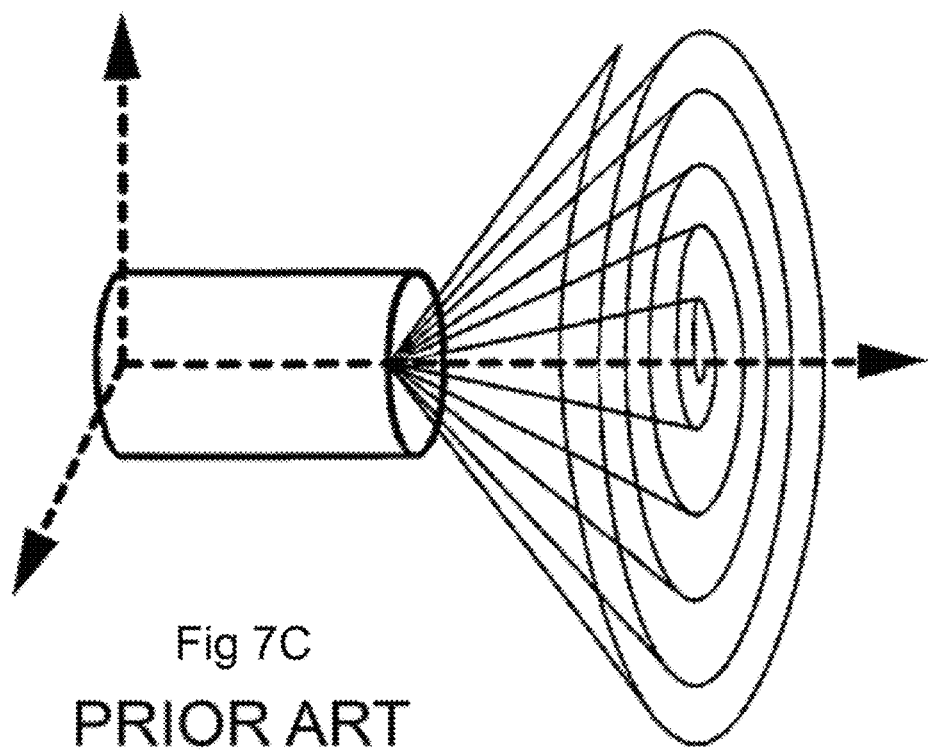

FIG. 7A depicts the first embodiment incorporating a 2D texture map 11 (corresponding to a single angle 'phi' (Φ)) combined with the representation of a 3D reconstruction 12. In this example, the three dimensional data lying outside the textured conical surface 11 has been excluded allowing visualization of the 2D image data 11 on the outside surface. This exclusion region is based on all image data represented at cone angles larger than that associated with the selected 2D imaging frame. This cone angle can be referred to as a clipping angle. Orienting the base of the cone 13 towards the observer facilitates viewing of the reconstructed 3D representation of image data on the inside of the conical surface. In this case, the 2D texture-mapped image has been acquired using the scanning pattern depicted in FIG. 7B. The imaging data frame representation 11, mapped to the surface of a cone as depicted in FIG. 6B, is positioned on the surface of the 3D conical volume representation such that imaged anatomical structures shown in the 2D imaging data 11 frame are aligned with their counterparts shown in the conical volume representation 12.

Figure 7D:
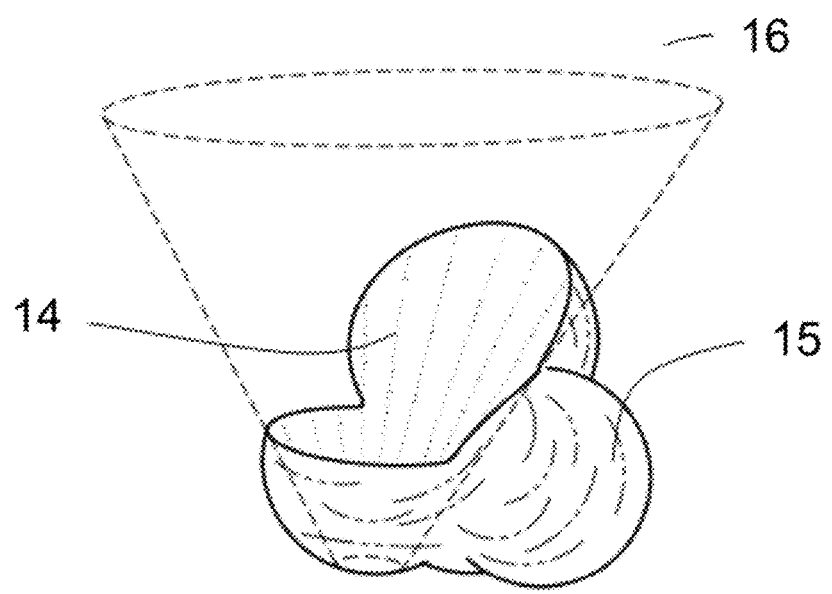

FIG. 7D depicts a similar embodiment incorporating a 2D texture map 14 with a reconstructed 3D representation 15. In this example, the three dimensional data occupying the interior of the cone (corresponding to values of 'phi' (Φ)) less than that of the selected 2D imaging frame) has been excluded. The 3D conical volumetric representation of imaging data lying outside the surface of the cone 15 (corresponding to values of 'phi' (Φ)) greater than that of the selected 2D imaging data frame) is now visible. This exclusion is based on all data at cone angles less than that associated with the selected 2D texture map 14. Again, this cone angle can be referred to as a clipping angle. Orientating the base of the cone 16 towards the observer allows observation of the 2D image data frame mapped onto the cone's interior surface. Again, the selected 2D image frame representation 14 is appropriately positioned on the interior surface of the 3D conical volume representation 15 such that the anatomical structures depicted in both representations are aligned.

The aforementioned composite visualization embodiments incorporated, by example, the identification of a single frame of imaging data to serve as the boundary separating the visible and non-visible portions of the conical volumetric representation. Potential embodiments may incorporate the selection of this boundary frame by either the operator or by the system itself. Any 2D frame of imaging data within the collected imaging data set may serve as the boundary frame, including those without a fixed angle 'phi' (Φ)) throughout the frame.

To facilitate visual continuity within the composite 2D-3D representation, embodiments may include a means of varying the transparency of all, or portions 29 of, the 2D and/or 3D component of the representation. This can be accomplished by associating an alpha channel with the depicted imagery where every image pixel of the representation contains both an intensity component (corresponding to a sample of image data) and an operator definable transparency component. Furthermore, transparency may also be used as the means for depicting the excluded regions of volumetric representations referenced in the preceding discussion centering on FIGS. 7A and 7D. Embodiments may facilitate adjustment of apply transparency levels through either the system or the operator.

Figure 9:
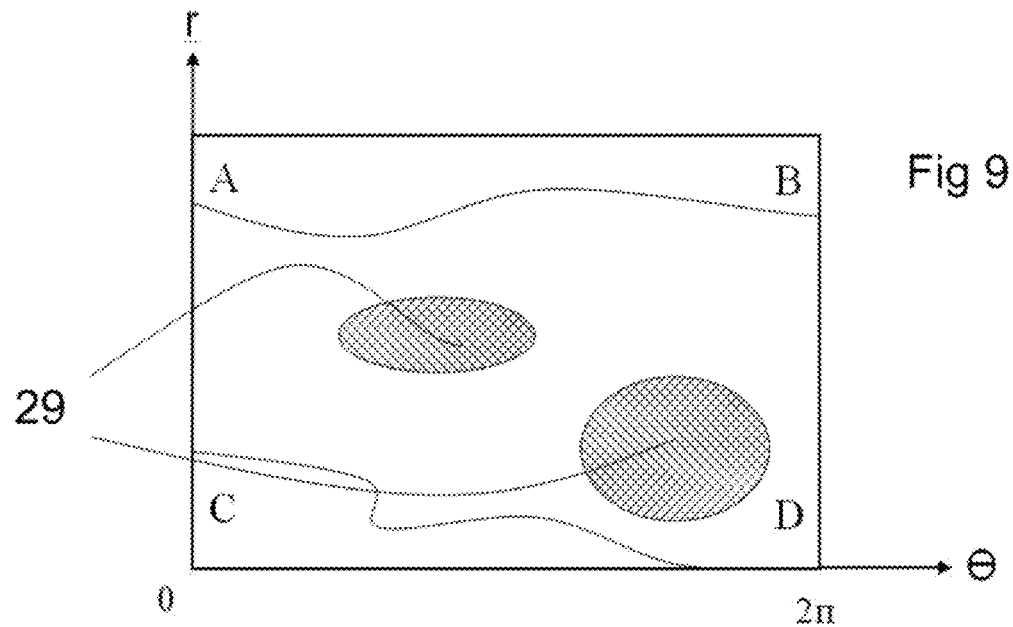
FIG. 9 depicts an example of imaging data for which regions are masked to permit transparent visualization through the conical surface.

To provide visual distinction between the 2D and 3D portions of the composite visualization, potential embodiments may also include a means of associating a color hue with all, or portions of, the 2D and/or 3D components of the representation. Color hue can be added to an image data visualization by assigning to each representative pixel a red, green and blue color channel value. The applied color hue may be varied by either the system or the operator and may be varied in conjunction with any applied transparency cue.

Where some embodiments may apply transparency and/or hue visualization cues uniformly to all pixels of the 2D and/or 3D portions of the composite representation, others may apply such visual cues on a pixel-by-pixel basis. An example embodiment is depicted in FIG. 9 where the transparency level (alpha channel value) and/or color hue (red, green and/or blue channel value) for every image pixel is determined by a function of that pixel's intensity (image data sample). In this case, bright pixels may be distinguished from dark pixels by differences in color hue and/or transparency. The operator may choose certain thresholds for pixel intensity values to reflect particular colors and/or transparency levels. Per-pixel transparency can be used to hide the depicted regions of tissue falling below a certain pixel intensity value thus revealing the depiction of tissue behind it. The inverse application of transparency values and/or color hue could be used to isolate particular regions from surrounding tissue. Embodiments would facilitate this per-pixel application of visual cues to portions of either the conical volume representation and/or the texture-mapped conical imaging frame.

Dynamic Volume Visualization

The nature of the imaging system described in U.S. Pat. No. 8,214,010 is such that the acquisition of image data in three dimensions is rate limited by the slowest acquisition axis. The temporal resolution of a volumetric image is defined by the time interval between updates of image data in a volumetric representation for a given set of spatial extents (ranges of the acquisition axes). As an example, a volumetric representation of an image data set for some range of values of 'r', 'theta' (Θ) and 'phi' (Φ)) of the imaging assembly is depicted in FIG. 1. The time interval needed to acquire fresh image data across the ranges of 'r', 'theta' (Θ) and 'phi' (Φ)) and process for display another volumetric representation defines the temporal resolution of the volumetric image. A low temporal resolution image is not well suited to the task of displaying fast moving structures within imaged anatomy. A means of increasing the temporal resolution for a set of acquisitions is to reduce the extents of the region to be scanned. For example, reducing the range of scanned angles 'phi' ($\Phi$)) in a system utilizing the coordinate system described in FIG. 1 would improve the temporal resolution of consecutively acquired image data sets. A similar effect would be achieved when reducing the range of scanned positions 'd' in a system utilizing the coordinate system described in FIG. 3. A combination of the above approaches may also be used.

Figure 10A:
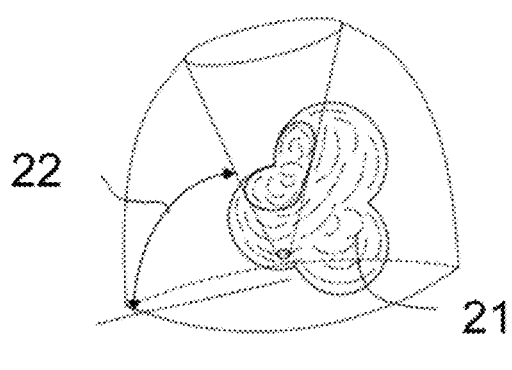
Figure 10D:
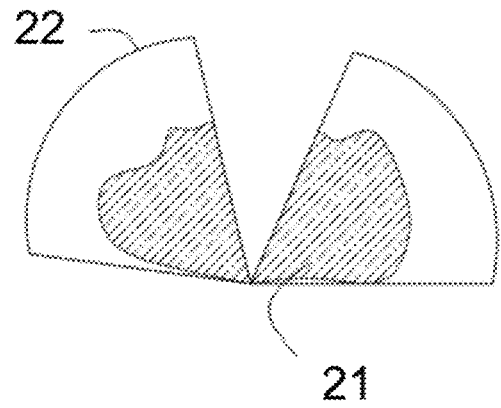

Understanding the effect of temporal resolution on the reconstruction of image data, it is advantageous to have a visualization embodiment that provides spatial awareness with high temporal resolution for an operator specified region of interest. The ability to combine a high spatial resolution 3D image representation with a high temporal resolution region of interest provides a means of accurately visualizing moving structures in the context of surrounding anatomy. FIGS. 10A through 10F depict an embodiment that achieves this. FIG. 10A shows a volumetric representation of a set of imaging data acquired over a relatively large region of the volume, in this case, a wide range of tilt angles 'phi' ($\Phi$) 22. FIG. 10D depicts a cross-section of the same volumetric representation. FIG. 10C depicts the volumetric representation composed with a smaller region of volumetric image data that is updated more frequently. Note that the range of angles 'phi' ($\Phi$) 24 is smaller than range used for the entire volume 22. FIG. 10F depicts a cross-section of the composite representation with the regions of high 27 and low 28 temporal resolution indicated.

Figure 10B:
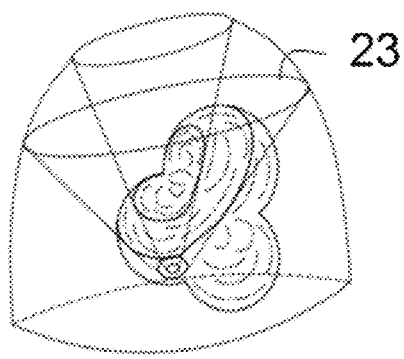
Figure 10E:
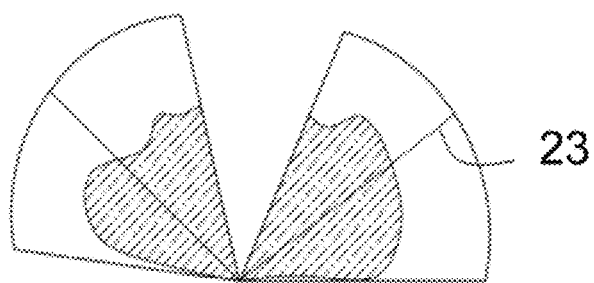

The composited region of interest can be of any size provided it is within the bounds provided by the imaging system. FIGS. 10B and 10E depict an embodiment in which the region of interest is a single frame of imaging data which, given the set of coordinate axes described in FIG. 1, is a single revolution of the imaging system about the axis 'theta' ($\Theta$). The size and position of the region of interest need not remain static between updates from the imaging system. Referring again to FIGS. 10B and 10E, there is shown an embodiment in which the region of interest described by the angle 'phi' ($\Phi$)) 23 continuously moves through the range of angles 22 defining the entire volumetric region and continuously updates the depicted representation as new image data frames are acquired from the imaging device.

Given that the nature of the imaging system described in U.S. Pat. No. 8,214,010 is such that the position of the imaging device will not necessarily remain fixed with respect to the imaged anatomy, it is advantageous for the system to be capable of determining when the position and/or orientation of the imaging device has changed as this affects the faithfulness of the composite visual representation, for example a user or system defined region of interest containing image data of a high temporal resolution 25. The imagery within this region will reflect movements of the imaging device more quickly than the surrounding regions of low temporal resolution 26. In other words, the imagery depicted in the region of interest may no longer spatially align with the imagery depicted in the surrounding contextual representation.

In a further embodiment there is provided an algorithm (corresponds to 35 of FIG. 11) for detecting spatial misalignment between regions of high and low temporal resolution. The algorithm is defined as follows: Begin by examining the image data associated with the representative portions touching the boundaries of the region of interest and, for each pixel pair occupying either side of the boundary plane, compute their relative difference in intensity (image data sample value). The sum of the differences for all such pixel pairs lying on the boundary plane is a metric quantifying how alike depicted imagery is on either side. When said metric is above an operator or system defined threshold, the spatial alignment may be considered unsuitable for continued display. In such cases, embodiments of the system may proceed by reacquiring a fresh image-set for the entirety of the contextual volumetric representation.

More comprehensive spatial misalignment detection algorithms may incorporate the image co-registration embodiments of Volume Registration and Motion Detection detailed elsewhere in this disclosure.

The flow chart in FIG. 11 presents the general series of steps an embodiment may follow to achieve the composite visualizations depicted in FIGS. 10A through 10F. The initial static volume is generated and displayed 31 after the system acquires image data 30 corresponding to a scanning field of view 22, after which an operator or system defined region of interest 18 is defined 32 and then updated repeatedly as the imaging system scans the constrained region. Due to motion of the imaging probe and/or surrounding anatomy, the imaging data corresponding to the region of interest is evaluated for spatial alignment with the initial static volume 35. If the spatial alignment is deemed adequate, the image data representation of the region of interest is composed with contextual volumetric visualization 36. If the spatial alignment is deemed to be poor, an image set to represent the extents of the entire contextual volumetric region is reacquired 31, thus starting the process over.

Embodiments of the invention need not retain the same region of interest between successive compositions of acquired image data. The system may update the region of interest 37 or retain the region defined by the user 38.

Additional embodiments incorporate the gated acquisition of imaging data to mitigate the effects of anatomical motion in the imaged region of interest. Such embodiments may incorporate an ECG signal to synchronize the acquisition image data with the cardiac cycle. Imagery acquired in such a fashion can yield volumetric representations of the heart at a single phase of the cardiac cycle. Alternatively, imaging data can be collected over several cardiac cycles thus enabling a four-dimensional reconstruction (multiple 3D volumetric representations varying with time). Embodiments may incorporate imaging data obtained through gated acquisition in some or all portions of the composite visual representation.

Additional embodiments may be provided which incorporate visual cues used to distinguish the imagery depicted within the region of interest from the imagery depicted in the contextual surroundings. Such visual cues may include the application of transparency and/or color to the visualized image data. Methods for applying said visualization cues would be the same as those described in previous embodiments and this application of said visual cues can be controlled by either the system or the user. As an extension of this, another possible embodiment may be provided in which the particular visual cue is a reflection of the amount of time that has elapsed since the visualized imagery was acquired by the imaging device. For example, the transparency (alpha value) of pixels constituting the imagery depicted in the contextual volume portion of the composite visualization is calculated as a function of the time from acquisition. Over time, as this portion of the visualization is not updated with new data, the constituent pixels of the representation become more and more transparent. Eventually these pixels may disappear entirely. The acquisition of fresh image data corresponding to the transparent regions of the representation would result in these regions being repopulated with opaque image data.

The application of visual cues are important in this embodiment as they convey the relative differences in temporal resolution between the different portions of the composite visualization. High temporal resolution regions are more likely to accurately reflect anatomical regions prone to movement. Conversely, depicted regions of low temporal resolution may become less trustworthy as the time interval from acquisition increases.

Volume Co-Registration and Motion Detection

Figure 12A:
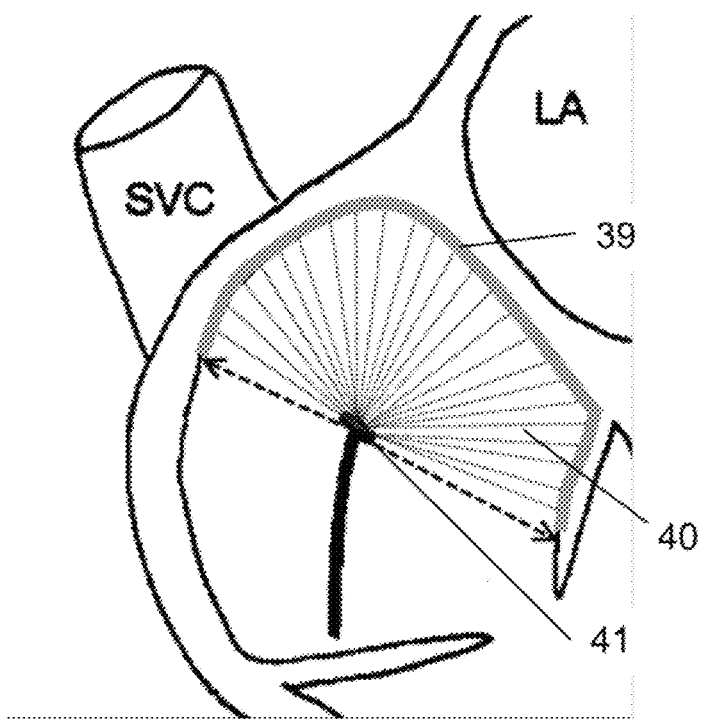

Motion of the imaging probe will affect the coherence between a static portions volume reconstruction and the dynamic nature of the imaging device. One method to provide increased coherence is to perform a registration between current imaging information and a static historical volume. In one embodiment (depicted in FIG. 12A), the catheter tip 41 is located inside a cardiac chamber. Begin by performing a "dense" scan 40 of the interior space thus acquiring a volume of high spatial resolution 45. For every line of image data acquired along r (as depicted in FIG. 1), for given angles of 'theta' ($\Theta$) and 'phi' ($\Phi$)), scan for the first point (starting from the origin) that represents cardiac tissue. Such a point could be determined by an increase of signal intensity from that which is characteristic of blood to that which is characteristic of heart tissue. The set of all points described by (r(i), 'theta' ($\Theta$), 'phi' ($\Phi$)) where 'i' represents the first incidence of cardiac tissue) collected for each r-vector defines the interior surface of the chamber 39. This collection of points may be stored as an attribute of the dense volumetric scan. The time required to perform this dense scan is typically long.

Figure 12B:
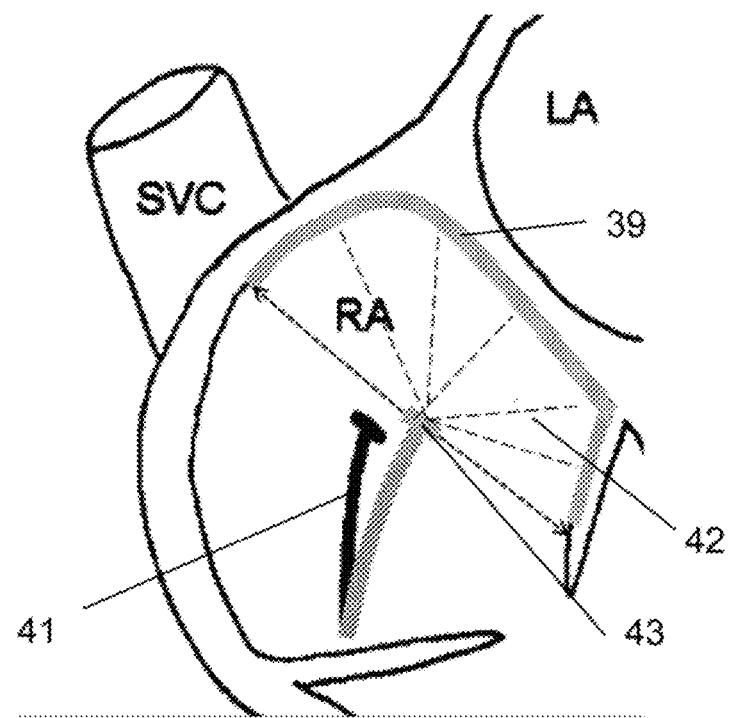

At some future point in time, in order to determine the location of the catheter tip relative to its location during the acquisition of the dense scan, the following steps may be performed (FIG. 13). Perform another volumetric scan 46 across similar ranges of r, 'theta' ($\Theta$) and 'phi' ($\Phi$)) but instead reduce the number acquired r-vectors by reducing the number of samples 42 across 'theta' ($\Theta$) and/or 'phi' ($\Phi$)) (FIG. 12B). Build another map of the interior chamber 39 in the same manner as before. The time required to perform this scan is reduced because the range of angles in 'theta' ($\Theta$) and/or 'phi' ($\Phi$)) can be traversed much more quickly. Furthermore, the time to compute this second map is less because of the reduced spatial resolution of the volume.

Having acquired data defining the interior surface of the cardiac chamber 39 in both a dense and sparse scan, the problem now becomes one of co-registering the two surfaces 47. In one embodiment, each surface is represented by a collection of points. A linear-least-squares best-fit approach can be used to determine the best positional correlation between two data sets, the product of which is the transformation (position and orientation) of the origin of one data set with respect to the other. This defines the change in location of the catheter tip from one volumetric scan 41 to the other 43.

An important consideration with co-registration is the notion of quality of fit. Continuing with the previous example, a byproduct of the linear-least-squares algorithm is the root-mean-square (RMS) sum of the total error between corresponding point pairs in the two data sets. The RMS error can be used as a metric for determining whether a registration of two volumes is acceptable and whether the updated position and orientation can be trusted. When a registration is deemed unacceptable, the system may determine that the relative positional information can no longer be trusted and that a new dense reference scan needs to be performed 50, 45.

As a refinement of the above example, an embodiment is provided which incorporates the detection of the transition into cardiac tissue along the r-dimension using a succession of r-vectors. Instead of defining the transition at a point, it can now be defined along an edge. The surface contour of the cardiac chamber can be expressed as a collection of edges rather than points. A modified co-registration algorithm can then be employed to determine the transformation between the acquired volumes and again yield an acceptance criterion indicative of the quality of the fit.

Refinements of the above embodiment may incorporate additional properties of the detected edge-space like strength (sharpness of image intensity change) or normal (orientation of the edge with respect to the acquisition origin). This additional information can be incorporated into the algorithm (performed in 47) used to determine the correspondence between the two image volumes.

An embodiment that incorporates multiple contour detection methods complete with multiple co-registration algorithms may be conceived. Each method would yield the co-registration transformation in addition to a co-registration accuracy metric. The average of the registration transformations from each algorithm weighed against its respective quality metric would provide a more robust estimate of the catheter tip position.

Potential embodiments need not be limited by the parameters used to acquire the sparse volumetric dataset. Rather than re-scanning the entire range, a much narrower range 44 of 'theta' ($\Theta$) and/or 'phi' ($\Phi$)) is scanned (as depicted in FIG. 12C) as a means of reducing the time required to perform a scan for the purpose of registration. The methodologies described above for identifying the interior surface of the cardiac chamber and registering that surface with another acquisition still apply when the second acquisition has reduced 'theta' ($\Theta$) and/or 'phi' ($\Phi$)) extents. Ultimately, embodiments may reduce the sub-volume down to just a single revolution about the 'theta' ($\Theta$) axis which, when tilt angle 'phi' ($\Phi$) is held constant, is representative of a single conical image frame. The aforementioned registration methods are still valid when considering a single imaging frame however it is expected that the likelihood of successfully registering smaller data sets to the larger contextual volume will be reduced.

Restricting the scanning region for the purpose of registration may have advantages beyond simply reducing acquisition time. For example the physician, through the application of some therapy, may physically alter appearance of tissue within the scanned field of view. If the contextual volume was acquired prior to this event then successive acquisitions, acquired for the purposes of co-registration, will no longer reflect the original tissue characteristics. In these cases, registration accuracy would improve if the tissue regions that were altered were excluded from the set of imaging data used for co-registration. One can imagine the operator, through the use of a 3D region of interest selection, manually defining the area or areas that have been altered and the system then ignores those regions when computing the next co-registration transform.

As a further refinement to the proposed registration embodiments, an embodiment includes incorporating information defining a set of "expected" catheter positions 51 based on the current known location of the catheter as well as its characteristic degrees of freedom 54. This additional information can be used to remove computed registration transformations from consideration 57 and/or reduce their weighting when considering them as a portion of the output from a multitude of registration methodologies 58. FIG. 14 depicts a flowchart detailing an algorithm making use of this type of information to filter the set of candidate catheter positions/orientations 56.

Finally, as an extension of the method defined in FIG. 14, an embodiment is provided which involves the incorporation of information additionally characterizing the expected trajectory of the imaging device 60. This information would ultimately come from the operator 61 as she would have knowledge of the procedure being performed. As an example, an embodiment includes the case where an operator wishes to perform a directed puncture or injection. The operator could indicate the intended position and orientation of the imaging device via the user interface of the imaging system at which point the system would determine the appropriate trajectory. The operator may also select a maneuver from a pre-programmed set of maneuvers, each of which could have its own means for determining expected position and orientation.

As mentioned elsewhere, the accuracy of three dimensional volume reconstruction is affected by cardiac motion and gating the acquisition of imaging data to portions of the cardiac cycle can improve accuracy. Similarly, co-registration accuracy is also effected by cardiac motion so employing gated acquisition techniques for co-registered image data sets will reduce co-registration error. Generally speaking, imaging sequences of low temporal resolution are affected by motion and benefit from gating algorithms known in the art, such as ECG gating, gating based on respiratory motion, etc.

Attempting registration in other anatomy, such as vessels, which lack the complexity to resolve ambiguities, could also be identified by an embodiment. This could be done through analysis of the high resolution static volume, determining if there is sufficient complexity for registration to be possible. Volume complexity can be quantified by inner surface smoothness, distribution of pixel edge strength and edge normal.

Sub-Volume Identification in Four-Dimensional Reconstructions

Of considerable use to physicians would be the ability to highlight or hide distinct anatomical structures of the heart (e.g., the interatrial septum) in three-dimensional imagery and not have to manually identify that same structure in subsequent frames of a 4D visualization. To facilitate this, the present disclosure provides a system that, when provided the extents of a three-dimensional sub-volume representation in one reconstruction, have the capability to automatically identify a sub-volume representation corresponding to the same portion of anatomy in subsequent reconstructions. Embodiments employing this capability must be able to account for slight variations in the size, location and orientation the structure of interest. These variations can be the result of movement of the imaging catheter and/or motion of the imaged cardiac structure itself.

Figure 15:
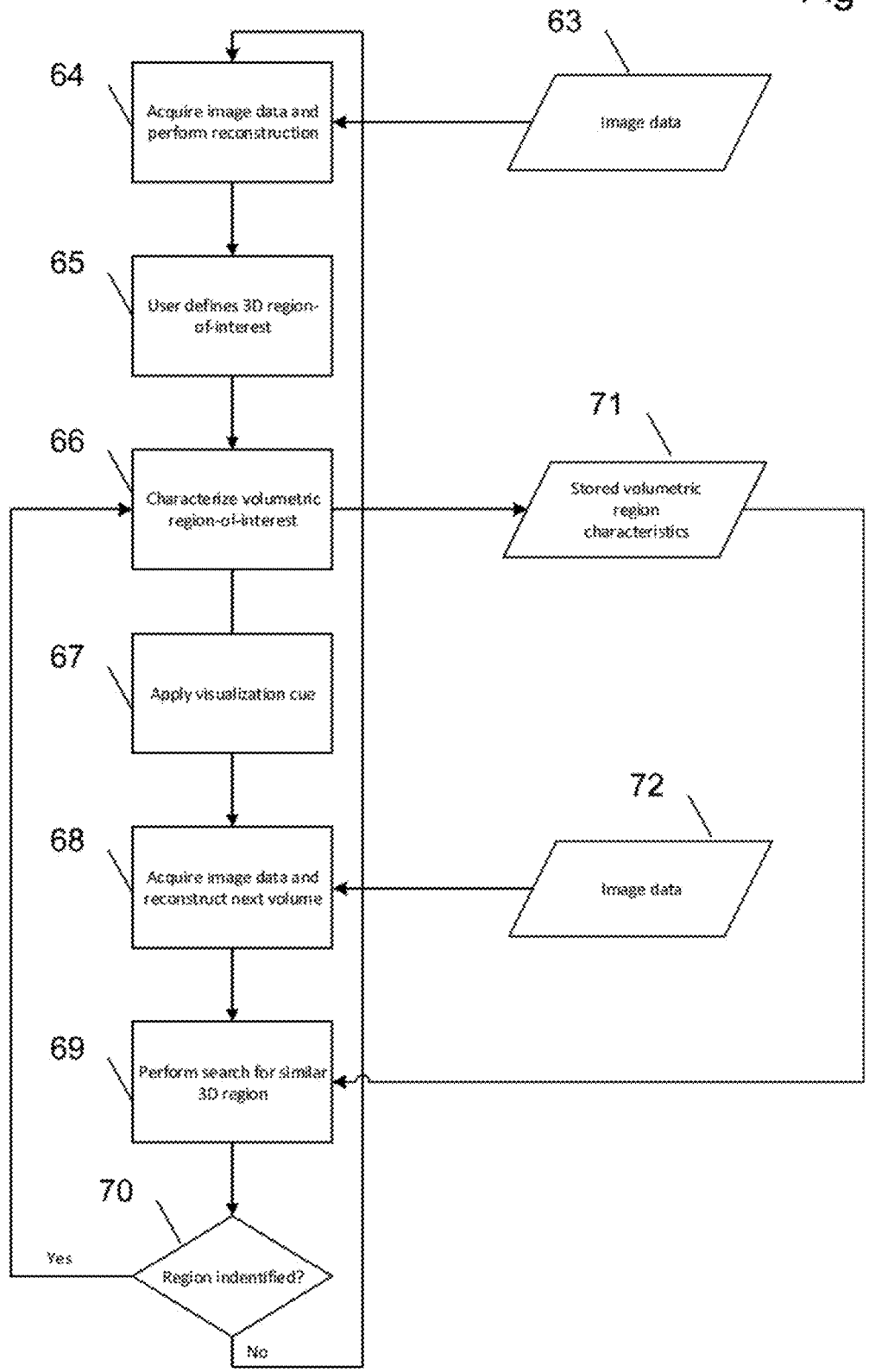
FIG. 15 shows a flow chart highlighting the important operations employed in an example embodiment where an operator identified volumetric sub-region is tracked in subsequent frames of a 4D reconstruction.

By way of example, the FIG. 15 shows another embodiment. The operator identifies a distinct volumetric region 65 within a reconstructed dataset 64 either manually (e.g., 3D region-of-interest selection) or through assisted selection aided by an automatic segmentation algorithm.

For the sub-step of automated segmentation, the present disclosure teaches the use of a recursive seed fill algorithm over a 3D pixel matrix employing a user or system defined tolerance. To begin, define the seed as 3D image pixel (voxel) selected by the operator. It is assumed that this voxel is located within the depicted boundaries of the region of interest within the volumetric representation. The algorithm looks at all voxels connected to the seed (neighbors) and 'colors' them if their intensity is equivalent (within the defined tolerance) to the seed. In a recursive fashion, the algorithm examines the neighbors of each colored voxel, coloring the neighbors when their intensity matches (again, with the defined tolerance) that of the seed. The colored region of connected voxels grows until no new voxels remain to be colored. The smallest enveloping bounds of the colored voxel region represents the system assisted selection. Adjusting the tolerance prior to performing the selection will affect how many voxels are colored and therefore the extents of the selection. Plainly, the intensity of the selected seed voxel will affect which voxels are included in the selection.

The identified sub-volume must have, at least approximately, an enveloping boundary characterized by a distinct region of differing voxel intensity. The system characterizes 66 the sub-volume by determining and processing its geometric center, center of mass, orientation (principle component axes), weighted orientation (weighted principle component axes), volume (voxel count) and/or dimensions along identified principle axes. The system highlights or hides 67 the region by applying either a hue or transparency visualization cue to the constituent sub-volume voxels.

Visual cues can be applied to the identified region of the volume representation in the same manner as described in previous embodiments of the present invention. The same types of visual cues, namely the application of color and/or transparency, would apply in the case of hiding or highlighting the volumetric region of interest. Similarly, potential use of the same cues on the inverse region (volumetric region not contained within the region of interest) is also possible. As in all other cases of applying visual cues to portions of the volumetric representation, the nature of the applied visualization is controlled by either the operator or the system. Finally, embodiments may employ an additional visual cue whereby the region of interest is positioned within the user interface such that it is always visible to the operator and never obstructed by other portions of the visualized representation or the other user elements of the user interface display. This feature of the embodiment is referred to as the centering view.

Subsequent volumetric scans are now collected 68 from more recently acquired image data 72. The search for the sub-volume matching the one previously characterized volume starts 69 at the characterized center (mass or geometry) location. Automatic segmentation is again employed in an attempt to identify a volumetric region enveloping the center point. To limit computational effort, the system can bound the search to roughly the same dimensions as previously the characterized volume, accounting for small variations in the sub-volume orientation. Successful identification of the target region will depend on how closely an identified sub-volume matches the characteristics (location, orientation, volume, dimensions) of the region of interest. Successful re-characterization of the target region is recorded and may be used as input for the search in the next image volume representation 71.

Additional embodiments may include an option to redefine the previously identified sub-volume characteristics with the results of the latest search 71 or some weighted average of each characteristic from the set of previous searches. Successful searches will result in the application of the same hide or highlight cue 67 to the depicted visual representation. In representations corresponding to subsequent image set acquisitions where the target region was not identified, the visual cue will not be applied. Failure to locate the region of interest in some number of (possibly zero) consecutively acquired image sets (or some minimum percentage of previously acquired image sets) results in the system abandoning future search attempts until such point that the operator reselects a region of interest 65.

The aforementioned embodiment is illustrative only and is not intended to limit the general mechanism depicted in FIG. 15. Refinements to the sub-region characterization can include more complex tissue segmentation algorithms and/or be tailored to search for cardiac structures of known morphology. Potential embodiments may, and likely will, incorporate other aspects of the present invention including sparse to dense volume co-registration, dynamic volume visualization and texture-map to clipped volume composite display.

Figure 17:
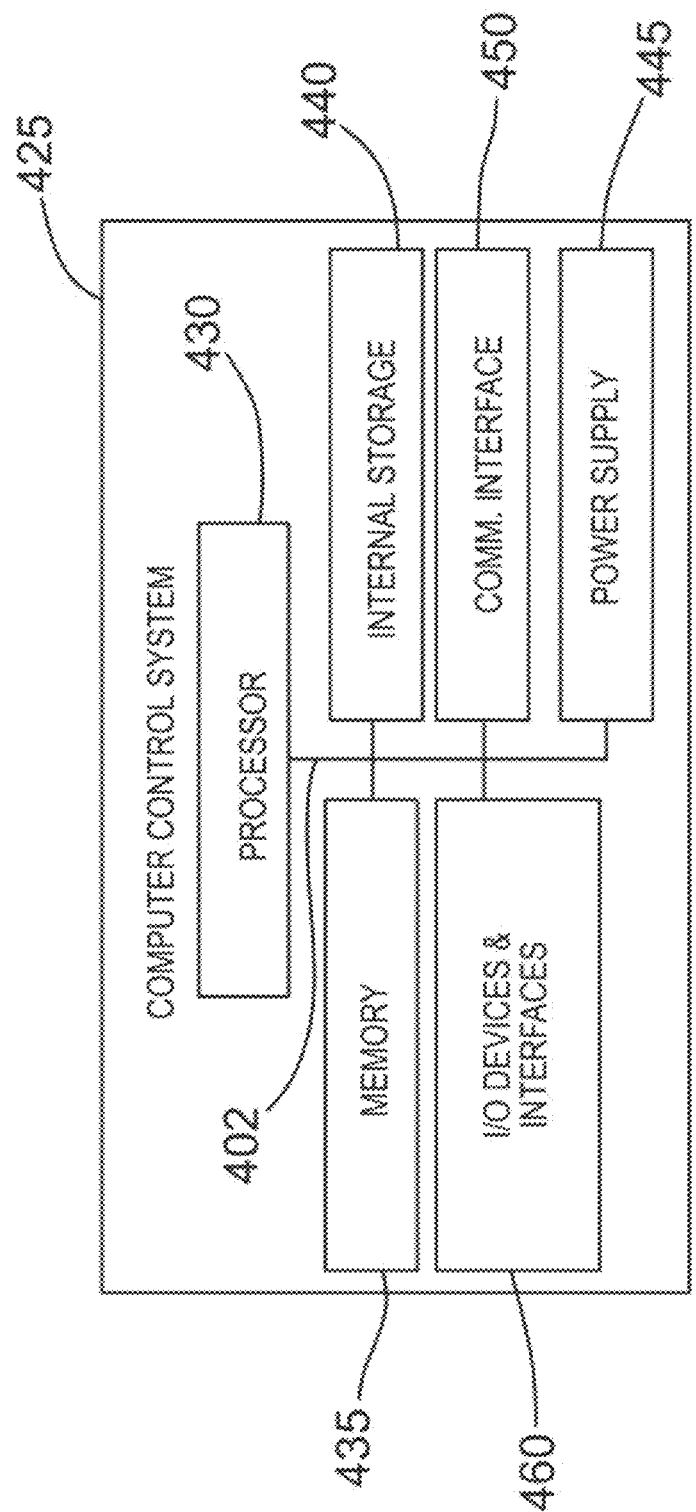
FIG. 17 shows an exemplary, non-limiting implementation of computer control system for implementing the planning and guidance method and system disclosed herein.

FIG. 17 provides an exemplary, non-limiting implementation of computer control system 425 for implementing the methods and systems disclosed herein, which includes one or more processors 430 (for example, a CPU/microprocessor), bus 402, memory 435, which may include random access memory (RAM) and/or read only memory (ROM), one or more internal storage devices 440 (e.g. a hard disk drive, compact disk drive or internal flash memory), a power supply 445, one more communications interfaces 450, and various input/output devices and/or interfaces 460 such as a user interface for a clinician to provide various inputs, run simulations etc.

Although only one of each component is illustrated in FIG. 17, any number of each component can be included computer control system 425. For example, a computer typically contains a number of different data storage media. Furthermore, although bus 402 is depicted as a single connection between all of the components, it will be appreciated that the bus 402 may represent one or more circuits, devices or communication channels which link two or more of the components. For example, in personal computers, bus 402 often includes or is a motherboard.

In one embodiment, computer control system 425 may be, or include, a general purpose computer or any other hardware equivalents configured for operation in space. Computer control system 425 may also be implemented as one or more physical devices that are coupled to processor 430 through one of more communications channels or interfaces. For example, computer control system 425 can be implemented using application specific integrated circuits (ASIC). Alternatively, computer control system 425 can be implemented as a combination of hardware and software, where the software is loaded into the processor from the memory or over a network connection.

Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

The invention claimed is:

1. A method of performing volumetric imaging and generating a composite visual display, the method comprising:
    employing an imaging probe comprising a rotatable imaging assembly to scan an imaging beam within a volume by performing scanning operations comprising:
        rotating the imaging assembly such that the imaging beam is rotated about a rotation axis, thereby varying a rotation angle of the imaging beam in a plane that is perpendicular to the rotation axis; and
    controlling the imaging assembly to vary a tilt angle of the imaging beam relative to the rotation axis;
    while performing the scanning operations, collecting a plurality of two-dimensional conical image frames, wherein each two-dimensional conical image frame has associated therewith a different tilt angle or a different range of tilt angles;
    selecting a two-dimensional conical image frame from the plurality of two-dimensional image frames for performing texture mapping;
    processing the plurality of two-dimensional image frames to generate a three-dimensional representation such that volumetric image data is excluded on a selected side of the selected two-dimensional conical image frame; and
    generating an image in which the selected two-dimensional conical image frame is texture mapped onto the three-dimensional representation.

2. The method according to claim 1 wherein the selected side is an inner side of the selected conical image frame.

3. The method according to claim 1 wherein the scanning operations comprise rotating the imaging beam about the rotation axis while continuous varying the tilt angle, and wherein the plurality of conical two-dimensional image frames comprise image data collected over different ranges of the tilt angle.

4. The method according to claim 1 wherein the image is generated such that the texture mapped image data is displayed with a selected color hue.

5. The method according to claim 1 wherein the three-dimensional representation is displayed with a selected color hue.

6. The method according to claim 1 wherein the image is generated such that the texture mapped image data is displayed with a selected transparency.

7. The method according to claim 1 wherein the three-dimensional representation is displayed with a selected transparency.

8. The method according to claim 1 wherein the selected two-dimensional conical image frame is defined by an operator.

9. The method according to claim 1 wherein the selected two-dimensional conical image frame is defined by an imaging system associated with the imaging probe.

10. The method according to claim 1 wherein an imaging modality of the imaging probe is ultrasound.

11. The method according to claim 1 wherein an imaging modality of the imaging probe is optical coherence tomography.

12. The method according to claim 1 wherein the plurality of two-dimensional conical image frames are acquired using gating techniques.

13. A method of generating a composite visual display from image data collected from an imaging probe, the imaging probe comprising an imaging assembly that is rotatable about a rotation axis and tiltable relative to the rotation axis, the method comprising:
   collecting a plurality of conical two-dimensional image frames during rotation of the imaging assembly about the rotation axis, wherein each two-dimensional conical image frame has associated therewith a different tilt angle or a different range of tilt angles;
   selecting a two-dimensional conical image frame from the plurality of two-dimensional image frames for performing texture mapping;
   processing the plurality of two-dimensional image frames to generate a three-dimensional representation such that volumetric image data is excluded on a selected side of the selected two-dimensional conical image frame; and
   generating an image in which the selected two-dimensional conical image frame is texture mapped onto the three-dimensional representation.

14. An imaging system for performing volumetric imaging and generating a composite visual display, the system comprising:
   an imaging probe comprising a rotatable imaging assembly;
   processing and control circuitry operatively coupled to the imaging probe, the processing and control circuitry comprising a processor and a memory, wherein the processor is configured to execute instructions stored in the memory for performing the steps of:
   controlling the imaging probe to scan an imaging beam within a volume by performing scanning operations comprising:
   rotating the imaging assembly such that the imaging beam is rotated about a rotation axis, thereby varying a rotation angle of the imaging beam in a plane that is perpendicular to the rotation axis; and
   controlling the imaging assembly to vary a tilt angle of the imaging beam relative to the rotation axis;
   while performing the scanning operations, collecting a plurality of two-dimensional conical image frames, wherein each conical two-dimensional image frame has associated therewith a different tilt angle or a different range of tilt angles;
   selecting a two-dimensional conical image frame from the plurality of two-dimensional conical image frames for performing texture mapping;
   processing the plurality of two-dimensional image frames to generate a three-dimensional representation such that volumetric image data is excluded on a selected side of the selected two-dimensional conical image frame; and
   generating an image in which the selected two-dimensional conical image frame is texture mapped onto the three-dimensional representation.

* * * * *